(12) United States Patent
Boettiger

(10) Patent No.: US 10,682,236 B2
(45) Date of Patent: Jun. 16, 2020

(54) KNEE JOINT ENDOPROSTHESIS

(71) Applicant: Aesculap AG, Tuttlingen (DE)

(72) Inventor: Roland Boettiger, Rietheim-Weilheim (DE)

(73) Assignee: Aesculap AG, Tuttlingen (DE)

( * ) Notice: Subject to any disclaimer, the term of this patent is extended or adjusted under 35 U.S.C. 154(b) by 123 days.

(21) Appl. No.: 15/964,345

(22) Filed: Apr. 27, 2018

(65) Prior Publication Data
US 2018/0243100 A1 Aug. 30, 2018

Related U.S. Application Data

(63) Continuation of application No. PCT/EP2016/075758, filed on Nov. 7, 2016.

(30) Foreign Application Priority Data

Nov. 6, 2015 (DE) .................. 10 2015 119 105

(51) Int. Cl.
*A61F 2/38* (2006.01)
*A61F 2/30* (2006.01)

(52) U.S. Cl.
CPC .............. *A61F 2/385* (2013.01); *A61F 2/384* (2013.01); *A61F 2/3868* (2013.01); *A61F 2002/30331* (2013.01); *A61F 2002/30364* (2013.01); *A61F 2002/30372* (2013.01); *A61F 2002/30481* (2013.01)

(58) Field of Classification Search
CPC ...... A61F 2/385; A61F 2/3868; A61F 2/3836; A61F 2/384; A61F 2/3845; A61F 2/389; A61F 2/38; A61F 2002/30481
See application file for complete search history.

(56) References Cited

U.S. PATENT DOCUMENTS

| | | | |
|---|---|---|---|
| 4,209,861 A | 7/1980 | Walker et al. |
| 4,340,978 A | 7/1982 | Buechel et al. |
| 5,755,804 A | 5/1998 | Schmotzer et al. |
| 5,824,096 A | 10/1998 | Pappas et al. |
| 5,964,808 A | 10/1999 | Blaha et al. |

(Continued)

FOREIGN PATENT DOCUMENTS

| | | |
|---|---|---|
| CN | 101627930 | 1/2010 |
| CN | 102076283 | 5/2011 |

(Continued)

*Primary Examiner* — Brian A Dukert
(74) *Attorney, Agent, or Firm* — Lipsitz & McAllister, LLC

(57) ABSTRACT

The present invention relates to a knee joint endoprosthesis having a tibial component and a femoral component and a hinge joint for coupling the tibial component and the femoral component so as to be pivotal about a rotational axis, which hinge joint comprises a first joint element and a second joint element coupled therewith so as to be rotatable about the rotational axis, wherein a connecting device is provided having at least one first connecting element and at least one second connecting element for connecting the first joint element to the femoral component, which connecting device defines a connecting position, in which the at least one first connecting element and the at least one second connecting element are engaged in a at least one of non-positive- and positive-locking manner, and an assembly position, in which the first joint element and the femoral component are fully separated from each other.

23 Claims, 14 Drawing Sheets

(56) References Cited

U.S. PATENT DOCUMENTS

Figure 1:
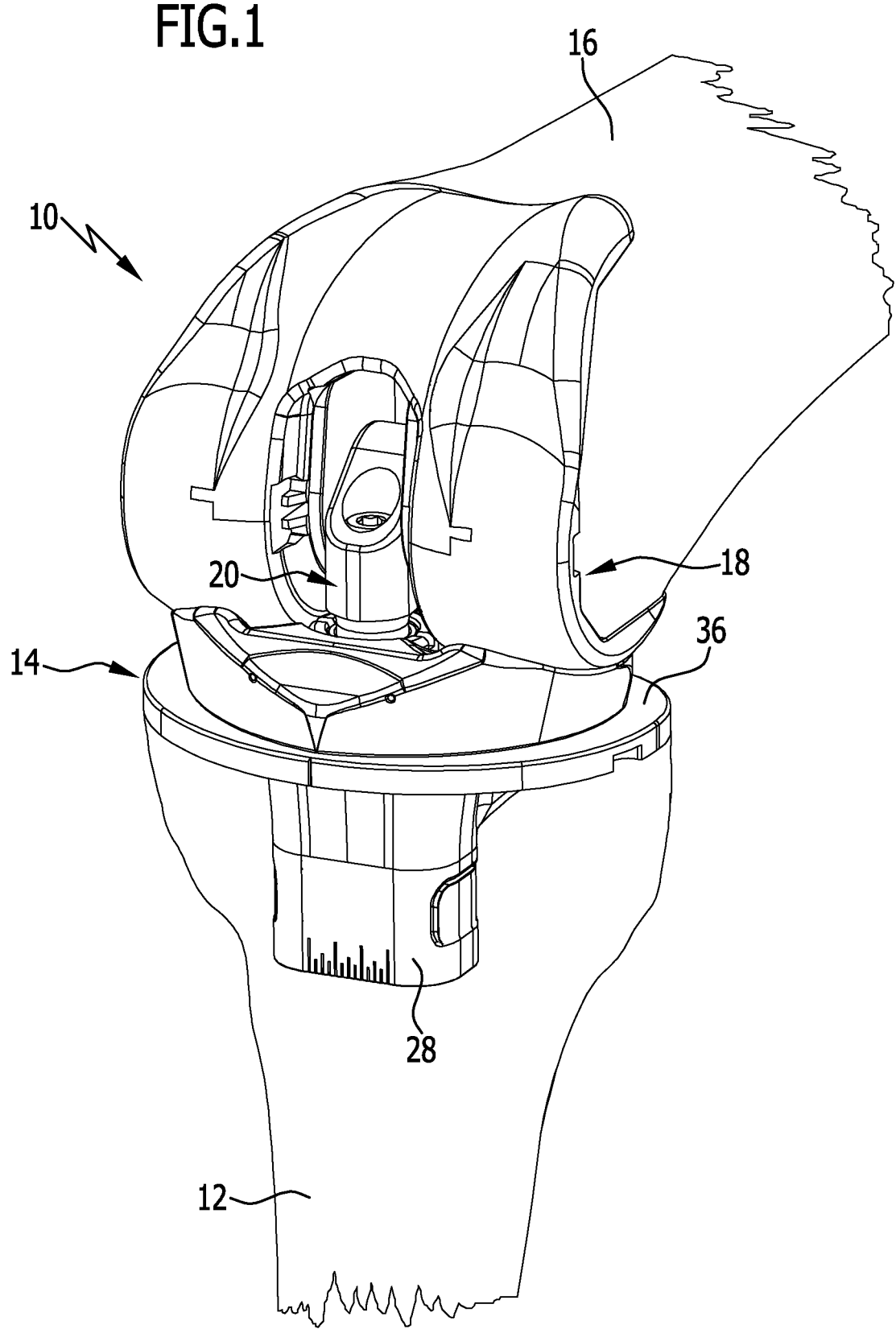

| | | |
|---|---|---|
| 6,485,519 B2 | 11/2002 | Meyers et al. |
| 6,984,249 B2 | 1/2006 | Keller |
| 7,918,893 B2 | 4/2011 | Romeis et al. |
| 8,163,028 B2 * | 4/2012 | Metzger .............. A61F 2/30721 623/20.15 |
| 8,545,570 B2 | 10/2013 | Crabtree et al. |
| 2002/0103541 A1 | 8/2002 | Meyers et al. |
| 2004/0186583 A1 | 9/2004 | Keller |
| 2004/0186584 A1 | 9/2004 | Keller |
| 2005/0107886 A1 | 5/2005 | Crabtree et al. |
| 2009/0088860 A1 | 4/2009 | Romeis et al. |
| 2009/0299482 A1 | 12/2009 | Metzger et al. |
| 2017/0020689 A1 | 1/2017 | Asmus et al. |
| 2017/0027706 A1 | 2/2017 | Hagen et al. |

FOREIGN PATENT DOCUMENTS

| | | |
|---|---|---|
| CN | 102596108 | 7/2012 |
| CN | 103153237 | 6/2013 |
| DE | 2122390 | 1/1973 |
| DE | 2522377 | 11/1976 |
| DE | 2906458 | 1/1984 |
| DE | 4102509 | 6/1996 |
| DE | 69206397 | 8/1996 |
| DE | 69323077 | 6/1999 |
| DE | 69324016 | 10/1999 |
| DE | 102009007724 | 8/2010 |
| DE | 102014204326 | 9/2015 |
| EP | 0716839 | 6/1996 |
| EP | 0923916 | 6/1999 |
| EP | 1226800 | 7/2002 |
| EP | 1381335 | 1/2004 |
| EP | 1132064 | 2/2007 |
| EP | 2042133 | 4/2009 |
| EP | 2213262 | 8/2010 |
| EP | 2272468 | 1/2011 |
| EP | 2272469 | 1/2011 |
| WO | 2015165955 | 11/2015 |

* cited by examiner

KNEE JOINT ENDOPROSTHESIS

CROSS-REFERENCE TO RELATED APPLICATIONS

This application is a continuation of international application number PCT/EP2016/076768 filed on Nov. 7, 2016 and claims the benefit of German application number 10 2015 119 105.9 filed on Nov. 6, 2015, which are incorporated herein by reference in their entirety and for all purposes.

FIELD OF THE INVENTION

The present invention relates to a knee joint endoprostheses generally, and more specifically to a knee joint endoprosthesis having a tibial component and a femoral component and a hinge joint for coupling the tibial component and the femoral component so as to be pivotal about a rotational axis, which hinge joint comprises a first joint element and a second joint element coupled therewith so as to be rotatable about the rotational axis, wherein a connecting device is provided having at least one first connecting element and at least one second connecting element for connecting the first joint element to the femoral component, which connecting device defines a connecting position, in which the at least one first connecting element or the at least one second connecting element are engaged in a non-positive- and/or positive-locking manner, and an assembly position, in which the first joint element and the femoral component are fully separated from each other, wherein the at least one first connecting element is associated with the first joint element or is arranged or formed thereon, and wherein the at least one second connecting element is associated with the femoral component or is arranged or formed thereon, wherein the connecting device defines a connecting direction in which the at least one first connecting element and the at least one second connecting element are moveable relative to each other for transferring the connecting device from the assembly position into the connecting position.

BACKGROUND OF THE INVENTION

A knee joint endoprosthesis of the kind described hereinabove is known in various embodiments. For example, one such is disclosed in EP 2 272 468 B1. In this knee joint endoprosthesis, the femoral component and the tibial component are implanted independently of each other, wherein the hinge joint is formed on the femoral component before the implantation. A coupling of the femoral component and the tibial component then takes place during the operation. A joint pin extension having a joint pin is hereby coupled by cooperative locking cones.

A disadvantage of the known knee joint endoprosthesis is in particular that for coupling the femoral component and the tibial component, the joint pin extension must be driven into the joint pin receiver provided on the joint pin in order to be able to ensure a secure connection. Upon said driving in, an impulse is also transferred to the tibial component which has already been implanted, so that there is a risk that it may unintentionally loosen.

SUMMARY OF THE INVENTION

In a first aspect of the invention, a knee joint endoprosthesis has a tibial component and a femoral component and a hinge joint for coupling the tibial component and the femoral component so as to be pivotal about a rotational axis. Said hinge joint comprises a first joint element and a second joint element coupled therewith so as to be rotatable about the rotational axis. Further, a connecting device is provided having at least one first connecting element and at least one second connecting element for connecting the first joint element to the femoral component. Said connecting device defines a connecting position, in which the at least one first connecting element and the at least one second connecting element are engaged in a at least one of non-positive- and positive-locking manner, and an assembly position, in which the first joint element and the femoral component are fully separated from each other. Said at least one first connecting element is associated with the first joint element or is arranged or formed thereon. Said at least one second connecting element is associated with the femoral component or is arranged or formed thereon. Said connecting device defines a connecting direction, in which the at least one first connecting element and the at least one second connecting element are moveable relative to each other for transferring the connecting device from the assembly position into the connecting position. Said connecting direction runs transversely, in particular perpendicularly, to the rotational axis.

BRIEF DESCRIPTION OF THE DRAWING FIGURES

Figure 2:
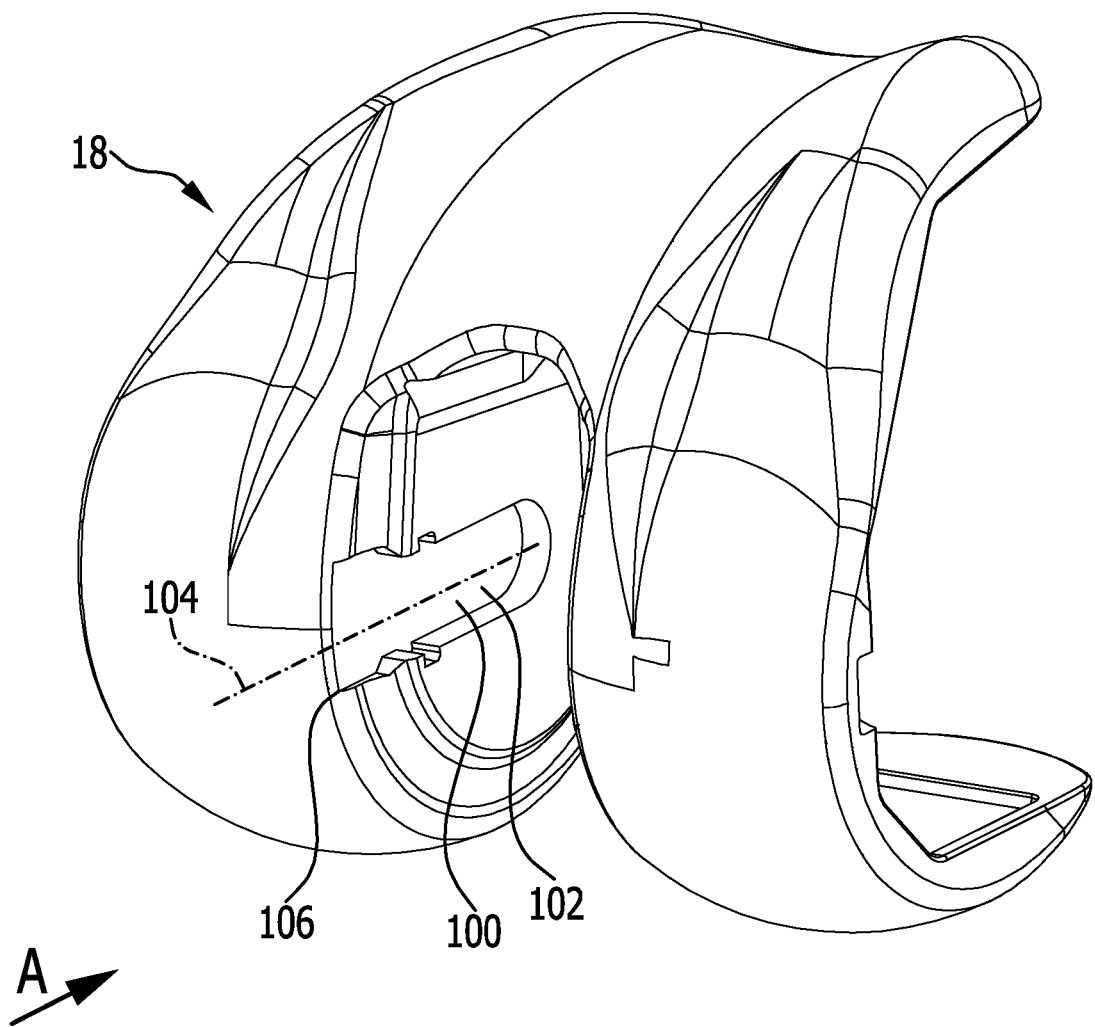
Figure 3:
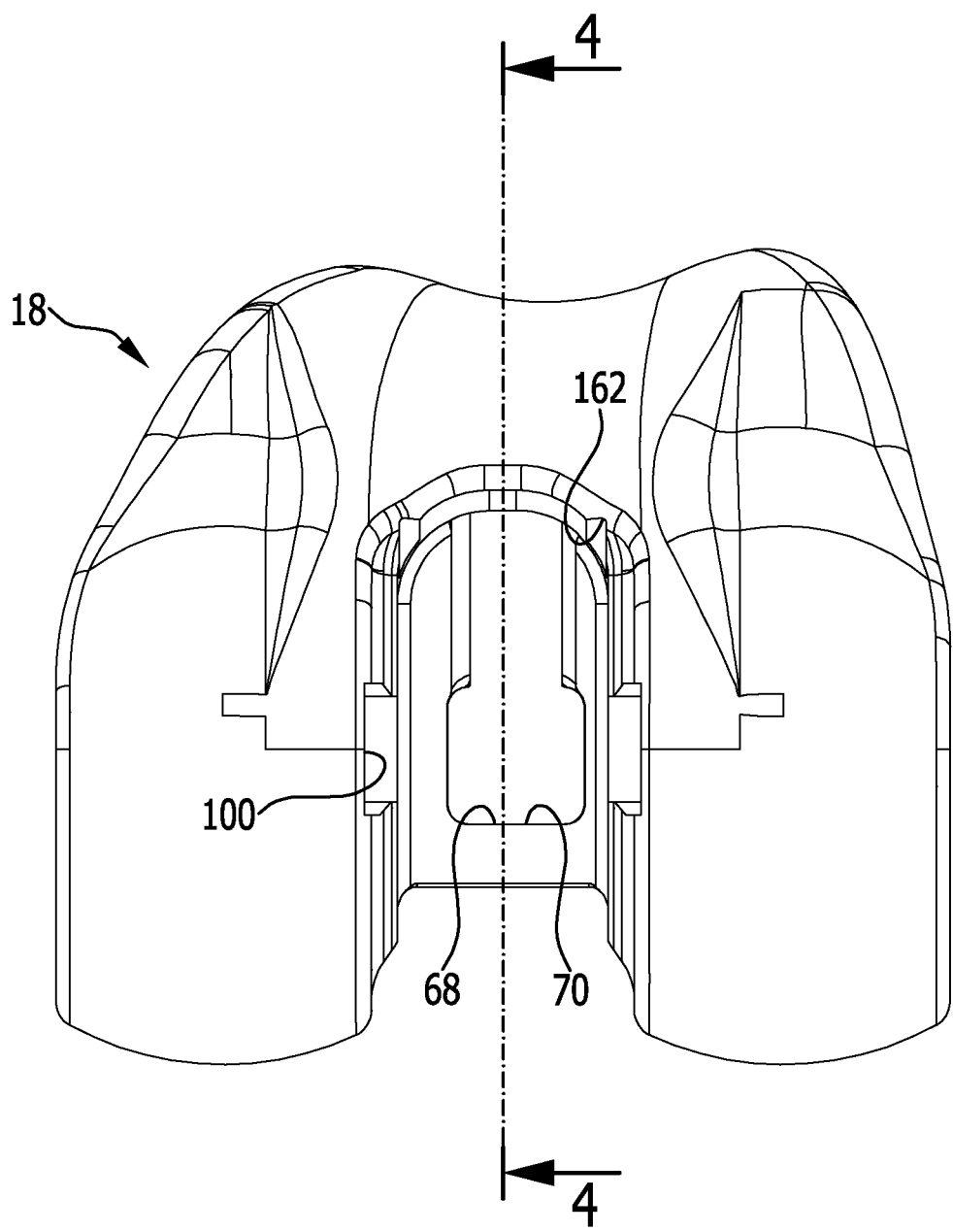
Figure 4:
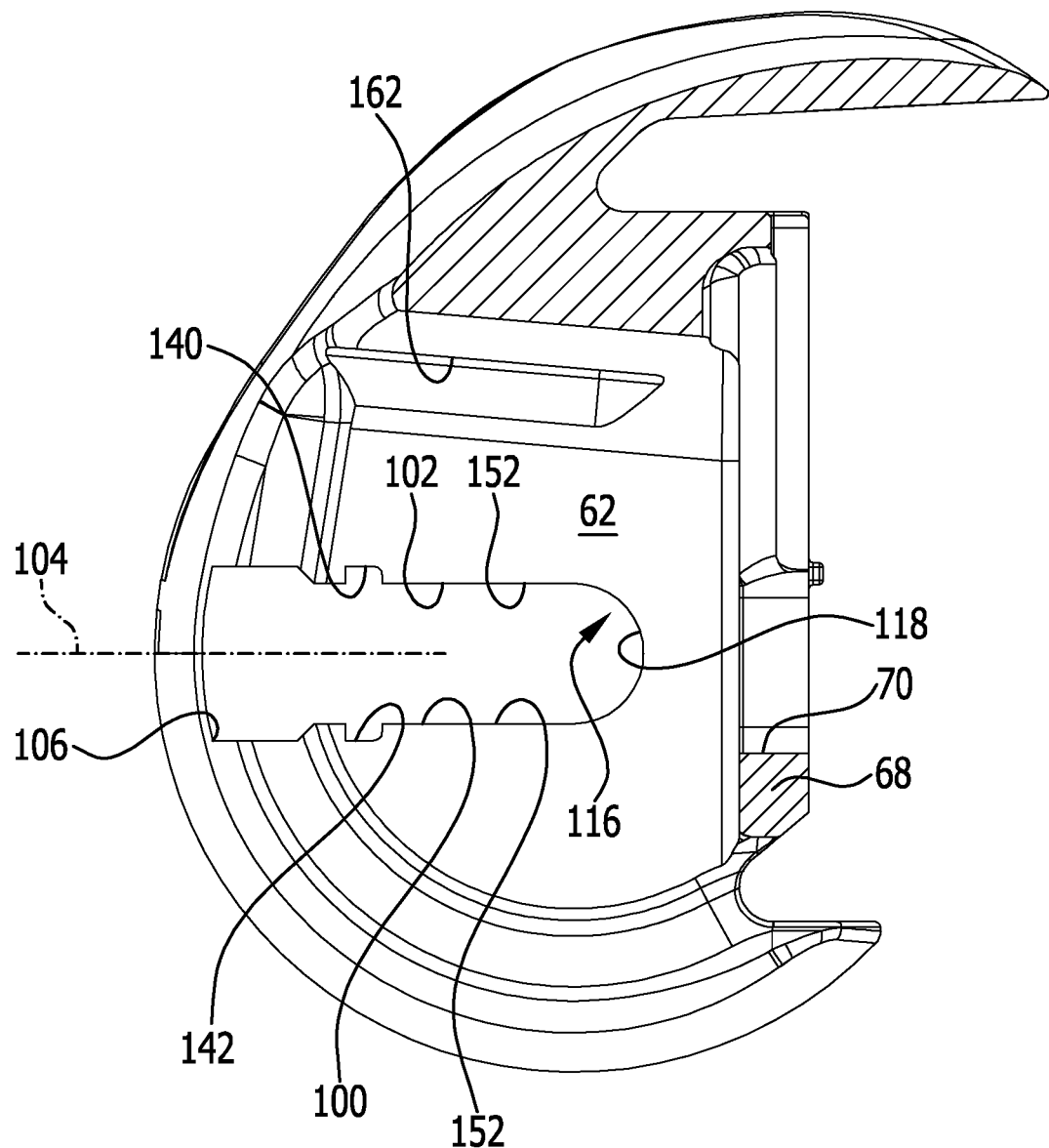
Figure 5:
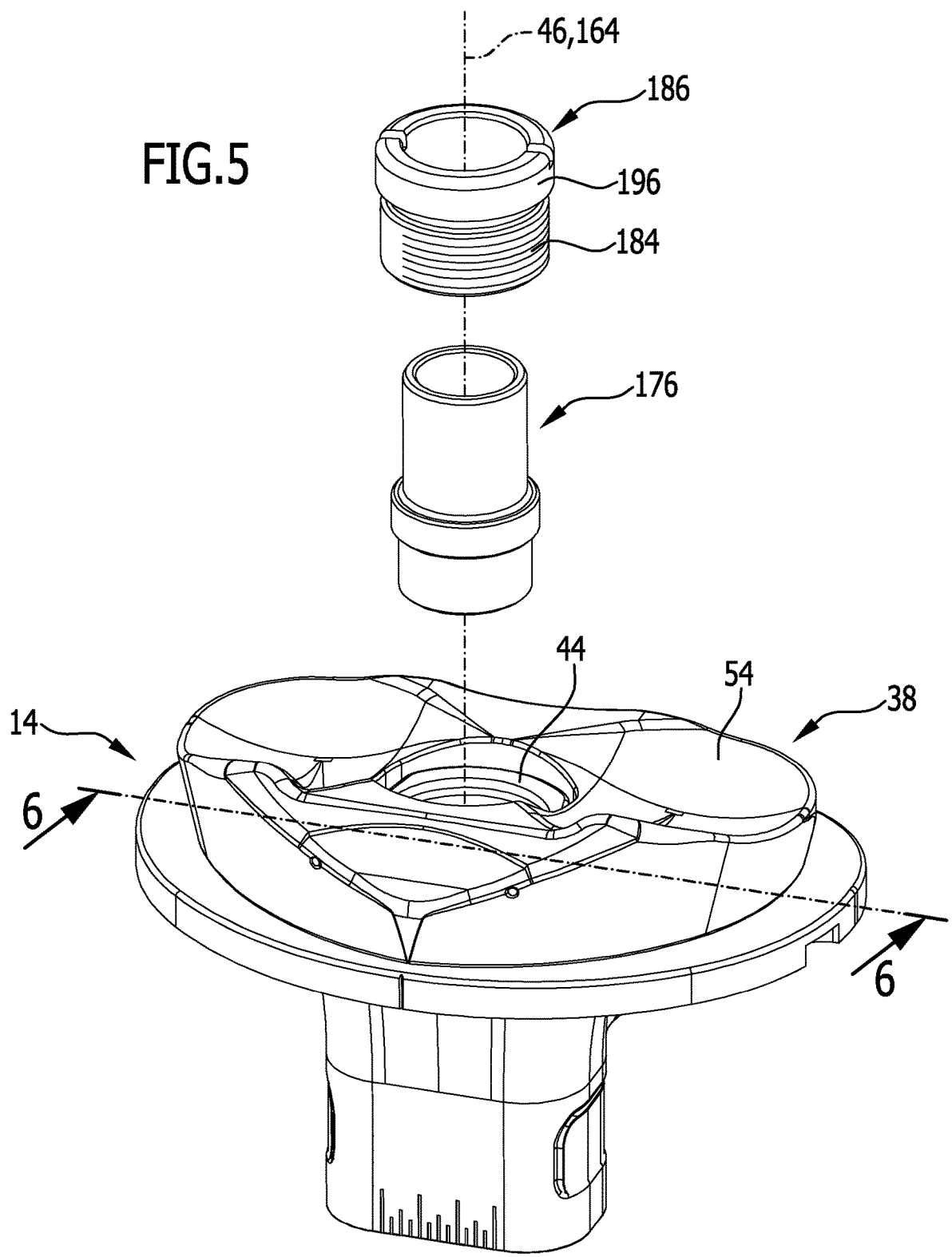
Figure 6:
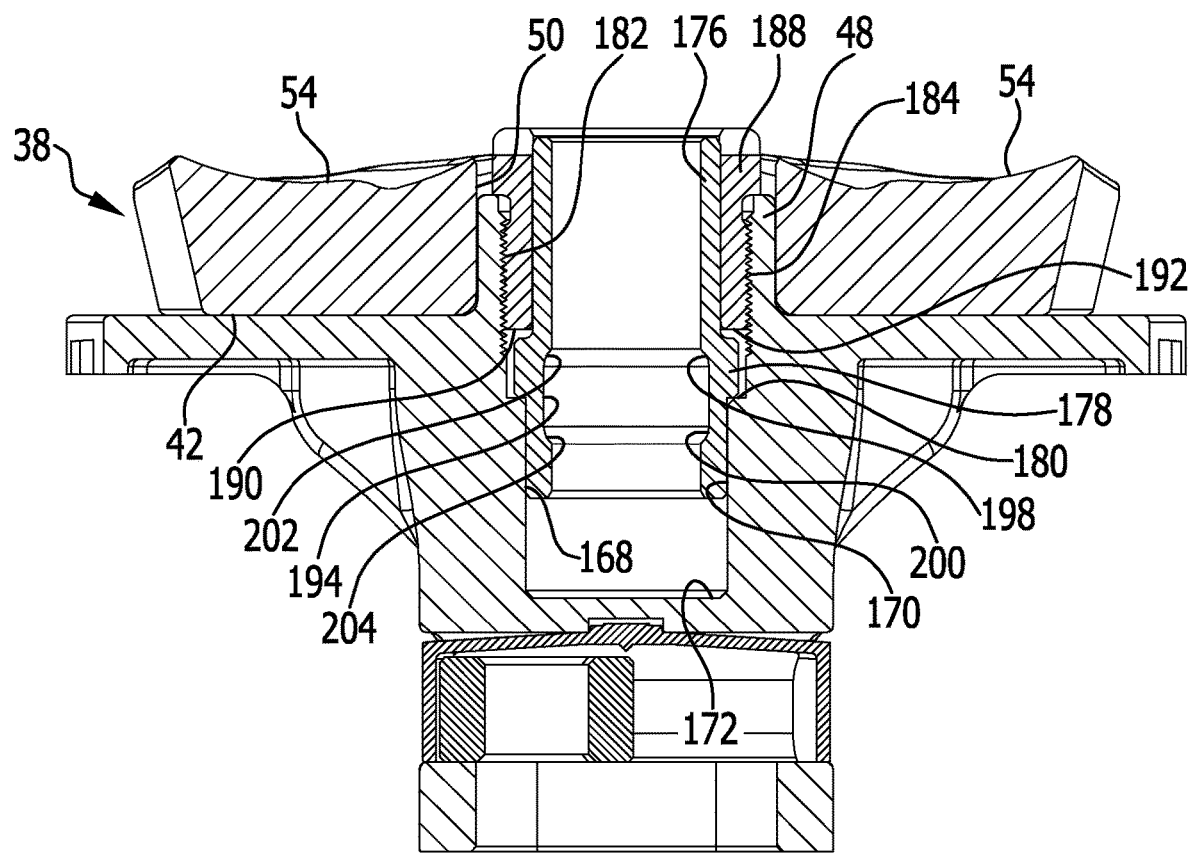
Figure 7:
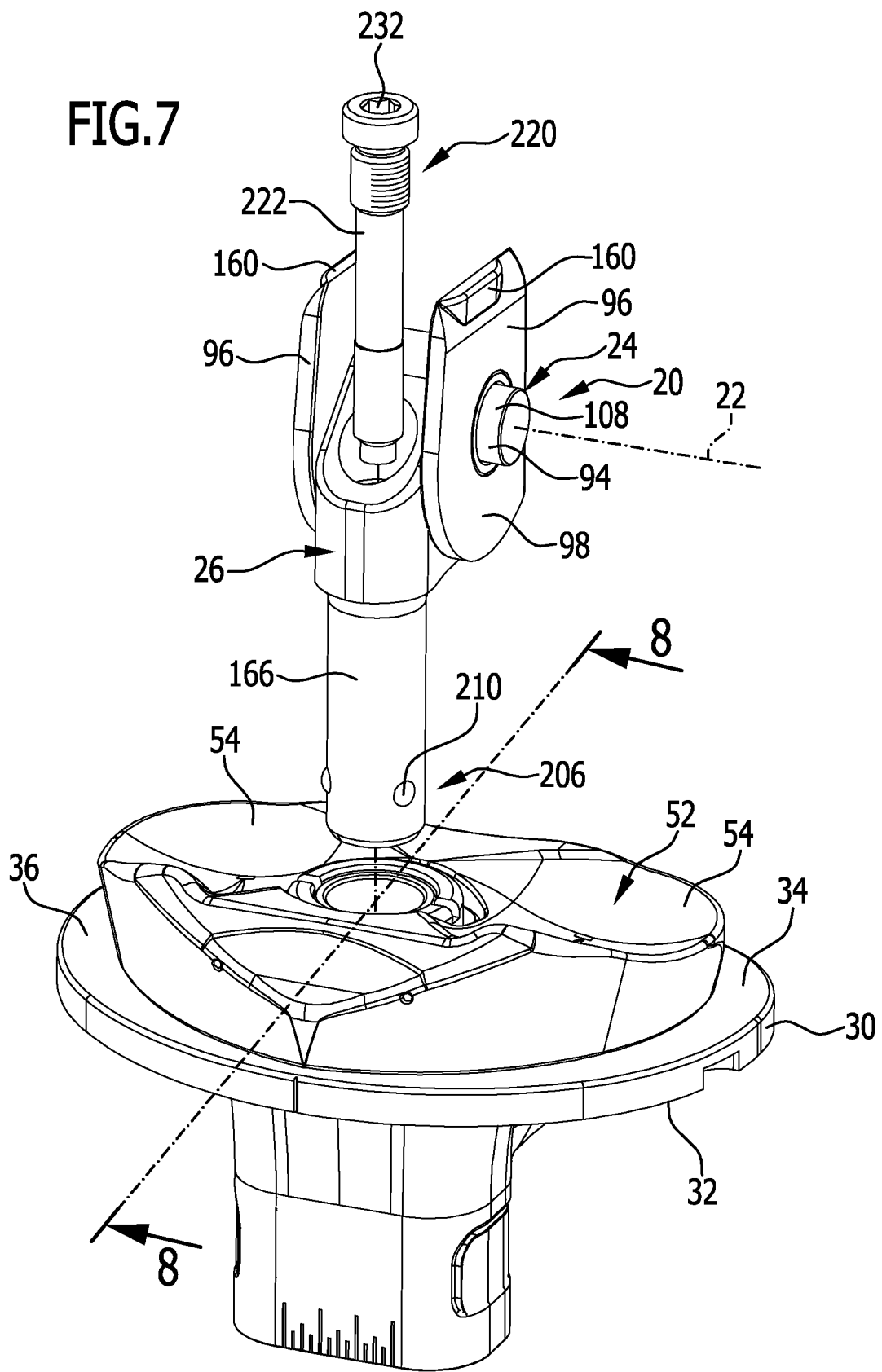
Figure 8:
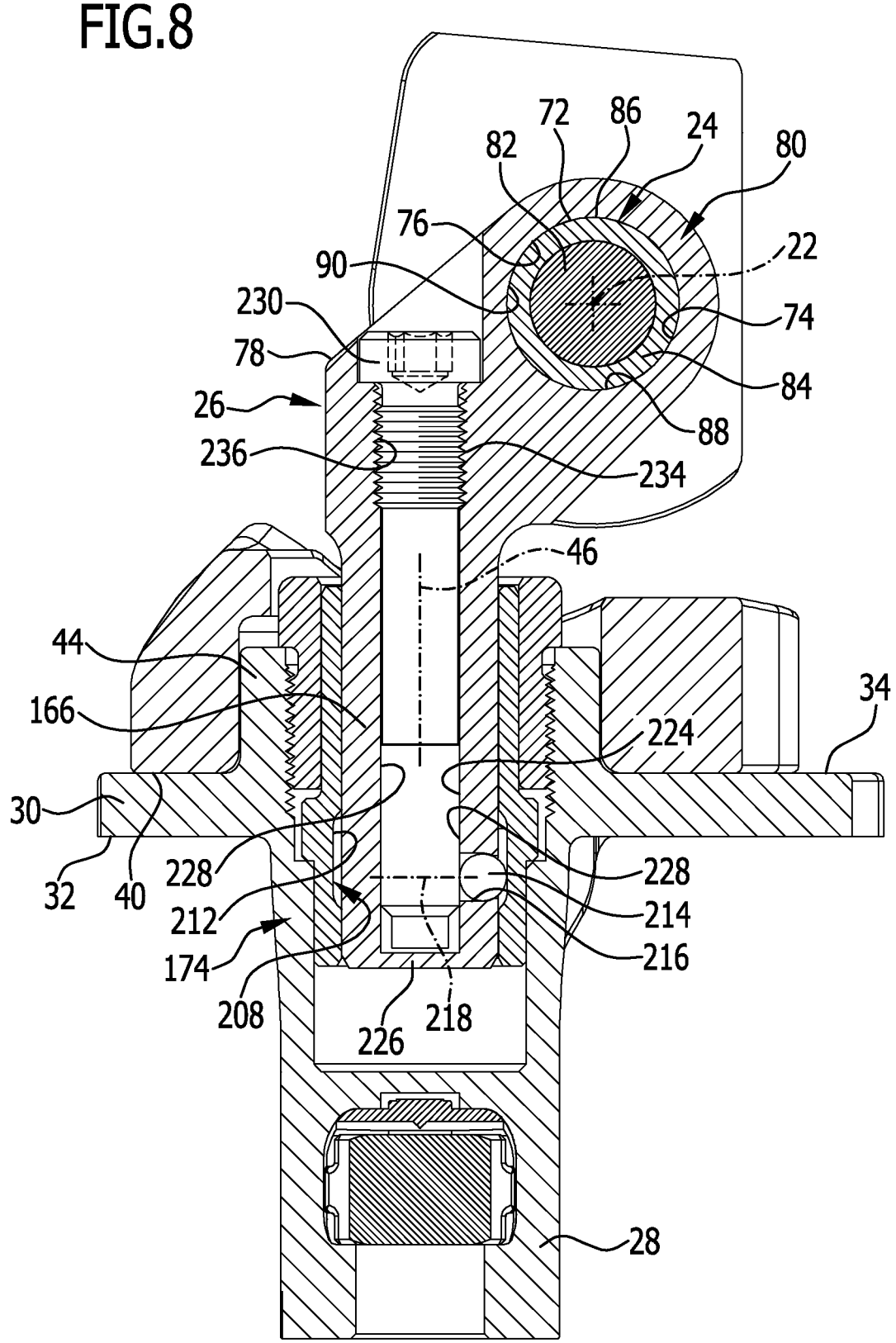
Figure 9:
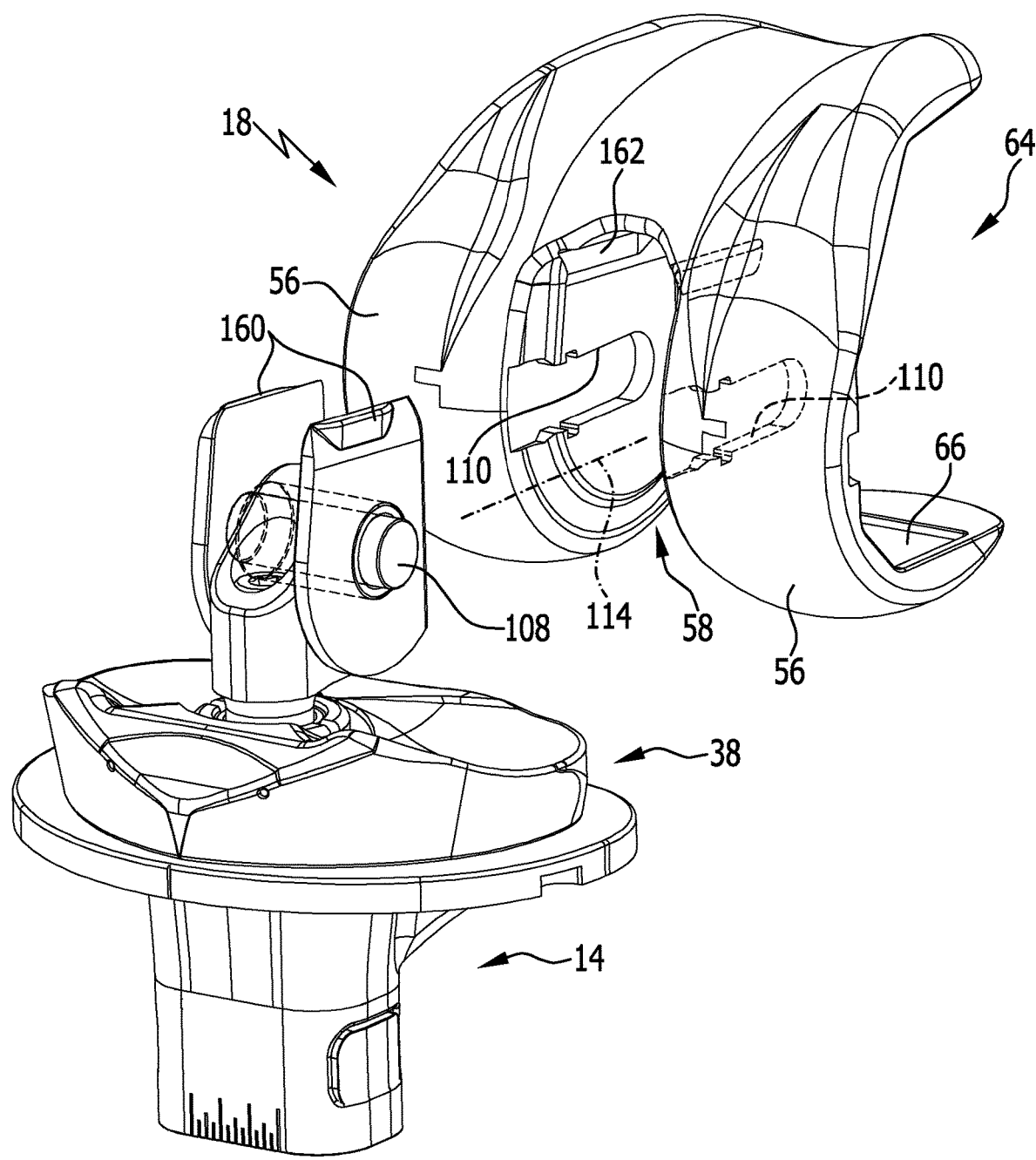
Figure 10:
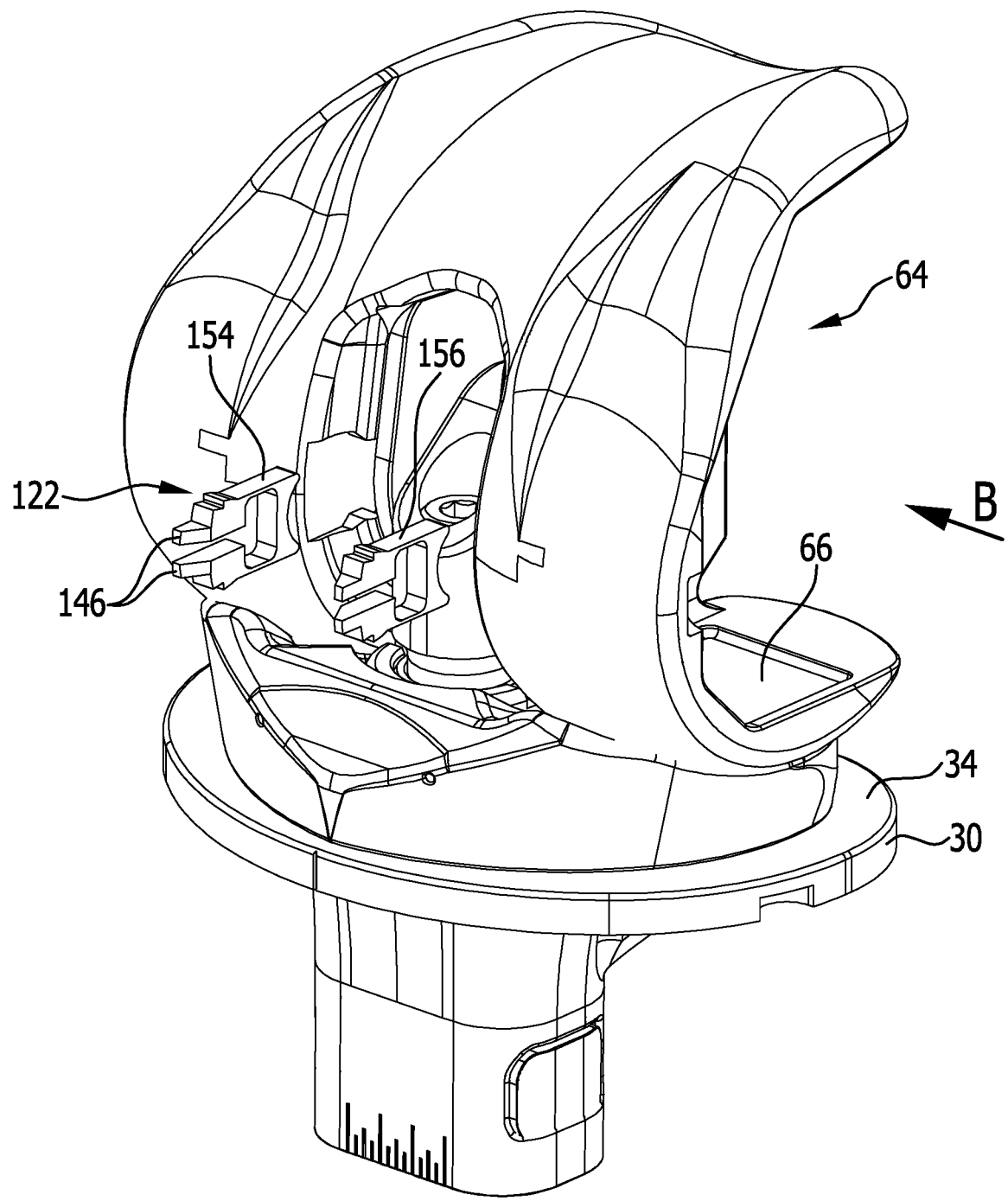
Figure 11:
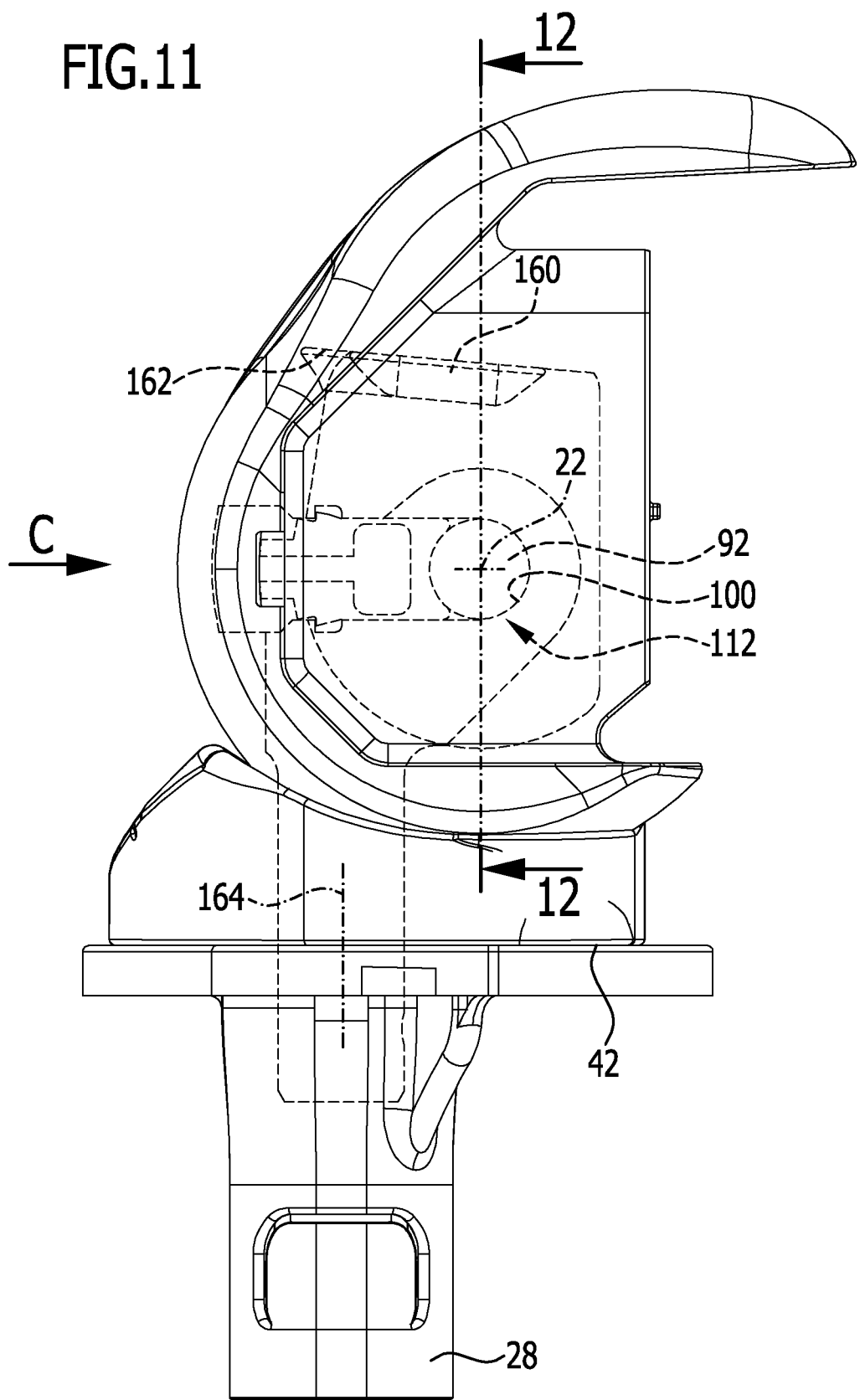
Figure 12:
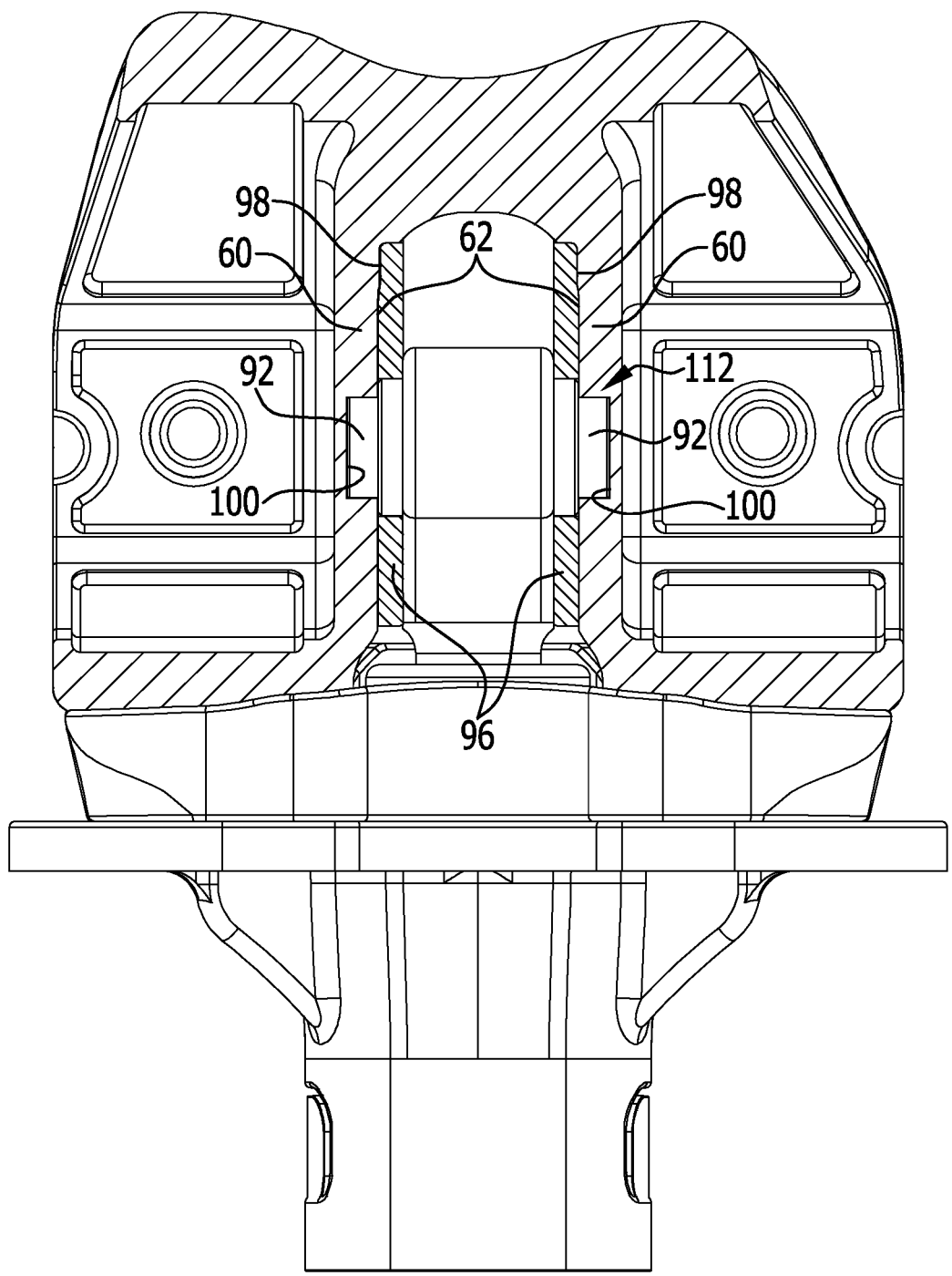
Figure 13:
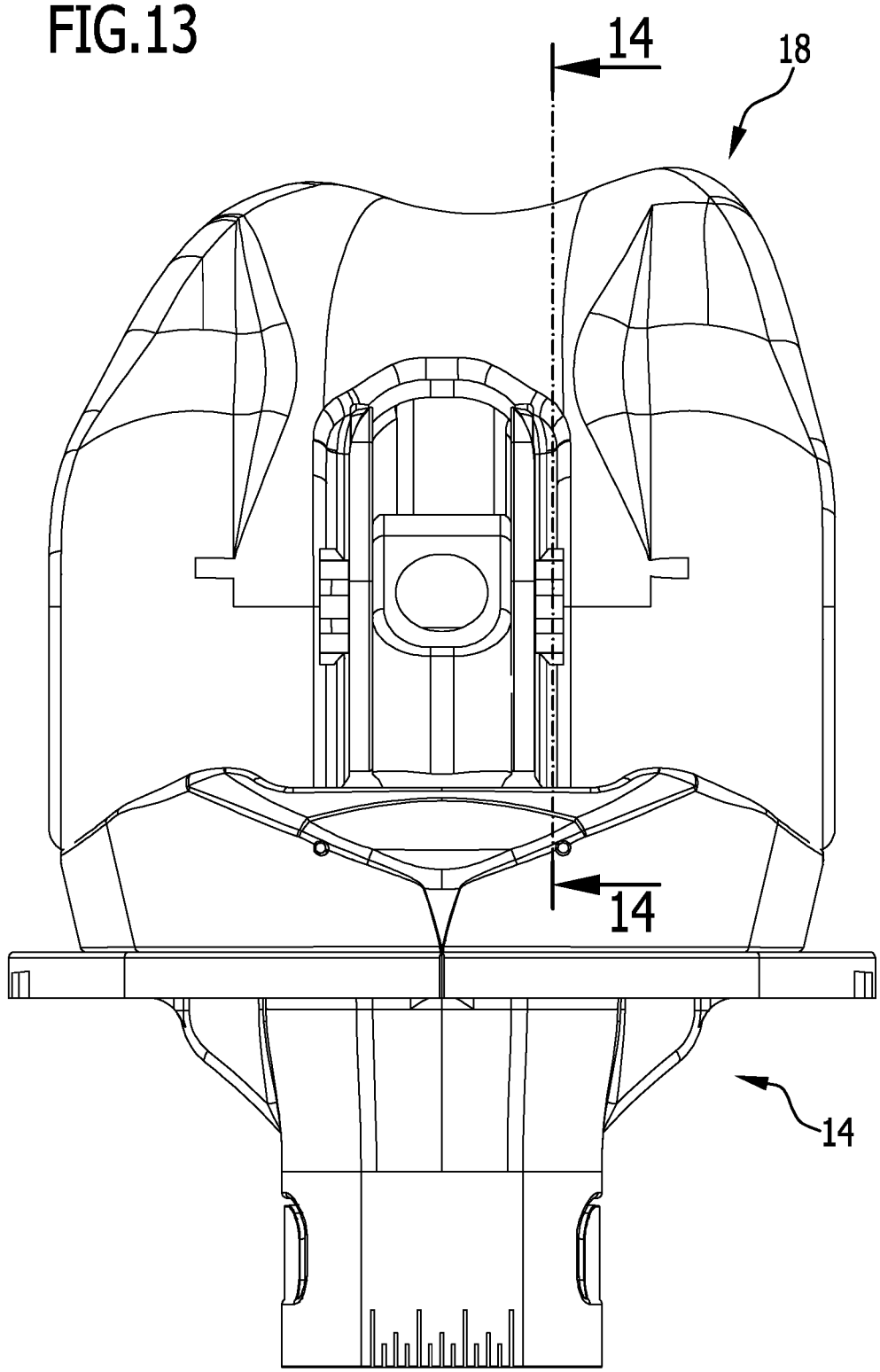
Figure 14:
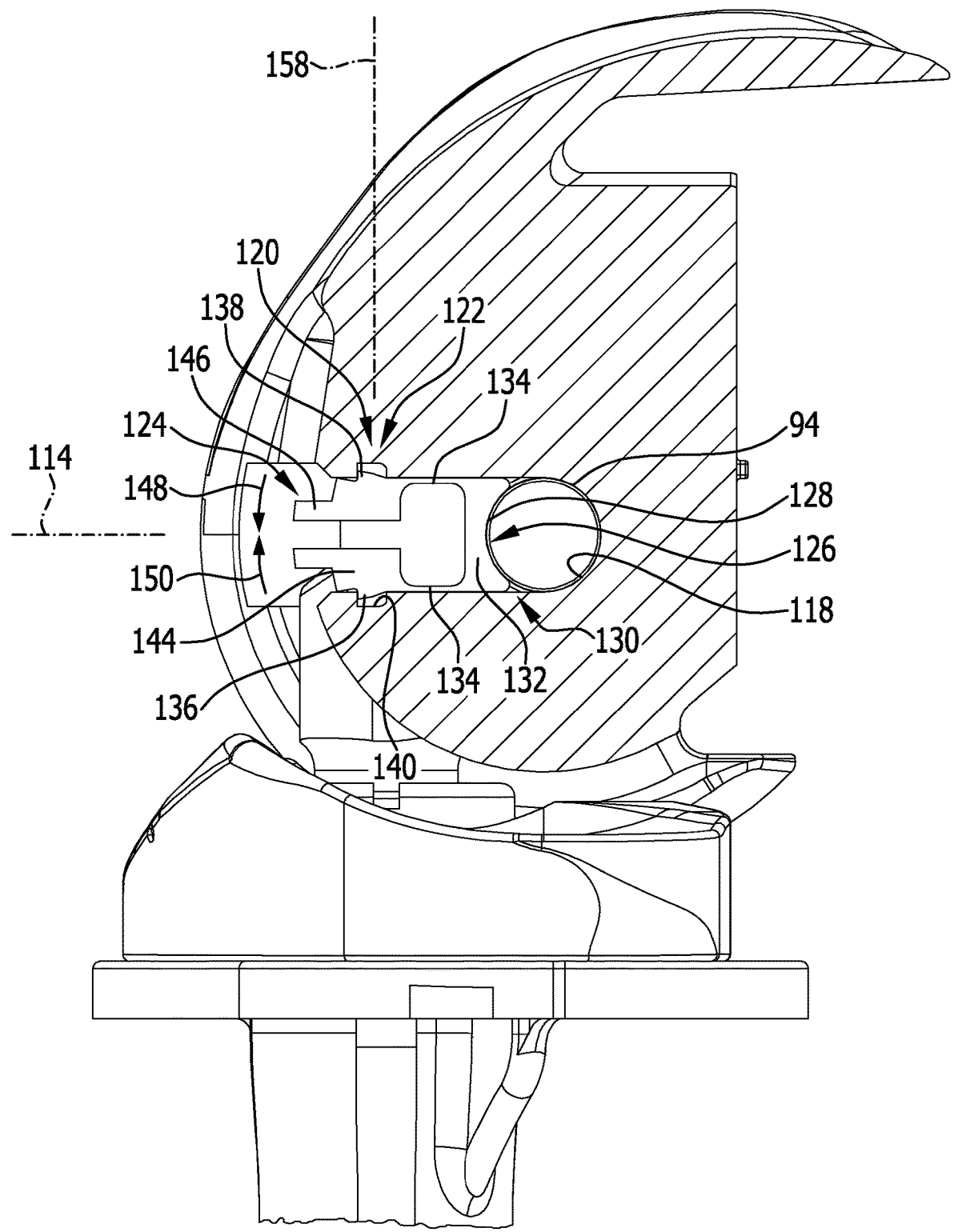

The foregoing summary and the following description may be better understood in conjunction with the drawing figures, of which:

FIG. 1: shows a perspective view of an embodiment of a knee joint endoprosthesis fixed to a femur and to a tibia;

FIG. 2: shows a perspective view of the femoral component of the knee joint endoprosthesis from FIG. 1;

FIG. 3: shows a view in the direction of the arrow A in FIG. 2;

FIG. 4: shows a sectional view along line 4-4 in FIG. 3;

FIG. 5: shows a perspective exploded view of the tibial component of the knee joint endoprosthesis from FIG. 1;

FIG. 6: shows a sectional view along line 6-6 in FIG. 5;

FIG. 7: shows a perspective, partial exploded view of the tibial component from FIG. 5 with a hinge joint;

FIG. 8: shows a sectional view along line 8-8 in FIG. 7;

FIG. 9: shows a perspective view of the knee joint endoprosthesis from FIG. 1 before coupling the first joint element and the femoral component;

FIG. 10: shows a perspective view of the knee joint endoprosthesis from FIG. 1 after coupling the femoral component and tibial component when using two securing elements;

FIG. 11: shows a partially broken view of the arrangement from FIG. 10 in the direction of the arrow B;

FIG. 12: shows a sectional view along line 12-12 in FIG. 11;

FIG. 13: shows a view of the arrangement from FIG. 11 in the direction of the arrow C; and FIG. 14: shows a side view along line 14-14 in FIG. 13.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a knee joint endoprosthesis having a tibial component and a femoral component and a hinge joint for coupling the tibial component and the femoral component so as to be pivotal about a rotational axis, which hinge joint comprises a first joint element and a second joint element coupled therewith so as to be rotatable about the rotational axis, wherein a connecting device is provided having at least one first connecting element and at least one second connecting element for connecting the first joint element to the femoral component, which connecting device defines a connecting position, in which the at least one first connecting element and the at least one second connecting element are engaged in a at least one of non-positive- and positive-locking manner, and an assembly position, in which the first joint element and the femoral component are fully separated from each other, wherein the at least one first connecting element is associated with the first joint element or is arranged or formed thereon, and wherein the at least one second connecting element is associated with the femoral component or is arranged or formed thereon, wherein the connecting device defines a connecting direction, in which the at least one first connecting element and the at least one second connecting element are moveable relative to each other for transferring the connecting device from the assembly position into the connecting position, wherein the connecting direction runs transversely, in particular perpendicularly, to the rotational axis.

The further development proposed in accordance with the invention enables in particular coupling the femoral component and the tibial component in particular intraoperatively by transferring the connecting device from the assembly position into the connecting position. For that purpose, unlike in the knee joint endoprosthesis known from EP 2 272 468 B1, for example, the first joint element is brought into engagement with the femoral component transversely to the rotational axis and not parallel to a longitudinal axis which is defined by the first joint element and which also defines the rotational axis. Due to this form of coupling of the femoral component to the tibial component, that is, in which the first joint element is coupled to the femoral component for connecting the mutually independently implanted femoral component to the tibial component, a force impact to the tibial component may be avoided. The connection relevant in particular for a coupling between the second joint element and the tibial component may then be made outside of the body of the patient by a surgeon. A coupling of the femoral component and the tibial component may be then achieved by a restricted movement of the two components relative to each other, namely by bringing the first and second connecting elements into engagement with each other by a movement in the connecting direction transversely to the rotational axis, in particular perpendicularly to the rotational axis. In addition, the proposed further development enables entirely foregoing locking cones, so that the risk of a loosening of such a locking cone connection after implantation may be impossible.

Preferably, the second joint element is held on the tibial component or is coupleable therewith. As a result, the hinge joint may already be arranged on the tibial component before implantation of the tibial component, i.e. just unlike in the knee joint endoprosthesis disclosed in EP 2 272 468 B1.

It is favorable if the connecting device is configured in such a way that it is transferrable from the assembly position into the connecting position after a mutually independent implantation of the femoral component and the tibial component. As already described above, this has the advantage that the femoral component and the tibial component may be implanted independently of each other. In addition, it may be prevented by means of the proposed further development that a force impact in the direction toward the tibial component needs to be exerted for coupling the femoral component to the tibial component.

The knee joint endoprosthesis may be constructed in a particularly simple and compact manner if a longitudinal axis defined by the first joint element defines the rotational axis. For example, the first joint element may comprise a cylindrical bearing bolt that, in the mechanical sense, forms a hinge axle of the hinge joint and that defines the rotational axis with its longitudinal axis.

It is advantageous if the at least one first connecting element is configured in the form of a connecting projection and the at least one second connecting element in the form of a connecting receiver, or vice versa. Connecting elements configured in that way may be brought into engagement and optionally out of engagement again in a simple manner.

The connecting receiver preferably extends in parallel to the connecting direction and has an insertion opening for the insertion of the connecting projection in parallel to the connecting direction. A connecting receiver arranged and formed in that way enables in particular inserting the first joint element with the at least one first connecting element into the connecting receiver transversely to the rotational axis.

In order to be able to ensure a secure connection between the first joint element and the femoral component, it is favorable if the knee joint endoprosthesis has two first and/or two second connecting elements.

In accordance with a preferred embodiment, provision may be made for the first joint element to be configured in the form of a hinge axle and for the second joint element to have a hinge axle receiver that is passed through by the hinge axle. A hinge axle in the sense of this patent application is a mechanical axle that is part of the hinge joint. It defines in particular the rotational axis, i.e. the mathematical axis about which the first and the second joint element may turn relative to each other.

The hinge joint may be constructed in a particular simple and compact manner if the hinge axle receiver is configured in the form of a through-bore.

The hinge axle and the hinge axle receiver preferably form a sliding bearing. Thus, a movement of the first and the second joint element relative to each other with minimal play may be specified.

Further, it may be advantageous if the hinge axle comprises a hinge axle core and a hinge axle sleeve arranged or mounted on the hinge axle core. Thus, for example, the hinge axle core may be formed out of a different material than the hinge axle sleeve. As a result, a sliding pairing between the hinge axle sleeve and the second joint element, for example, and, at the same time, a stability of the hinge joint may be optimized. The hinge axle sleeve may thus be made in particular out of a plastics material, for example polytetrafluorethylene (PTFE), the hinge axle core out of a biocompatible metal, for example an instrument steel.

The hinge axle sleeve and the hinge axle receiver preferably define the sliding bearing. An optimal sliding pairing may thus be formed between the hinge axle sleeve and the hinge axle receiver, wherein the hinge axle sleeve may be made in particular out of a suitable plastics material.

The knee joint endoprosthesis may be constructed particularly stably if the hinge axle core in the connecting position is engaged with the at least one second connecting element in a non-positive- and/or positive-locking manner. In particular, the hinge axle core may comprise the at least one first connecting element. For example, free ends of the hinge axle core may each form or define a first connecting element.

It is favorable if the hinge axle core has a circular, oval, or an angular, in particular a rectangular or hexagonal, cross section. In particular in the case of a non-circular cross section of the hinge axle core, a non-rotatable connection between the hinge axle core and the second connecting element and thus between the first joint element and the femoral component may be formed.

Further, it is advantageous if the hinge axle sleeve has a hinge axle receiver for accommodating the hinge axle core, and if the hinge axle core receiver has a free cross section corresponding to the hinge axle core. If the free cross section of the hinge axle core receiver is non-round like, for example, an oval or angular cross section of a hinge axle core, then a non-rotatable connection between the hinge axle sleeve and the hinge axle core may be achieved in a simple manner.

Favorably, the hinge axle core projects out of the hinge axle sleeve on both sides. This enables in particular using sections of the hinge axle core that project out of the hinge axle sleeve as first connecting elements for coupling or connecting the hinge axle core and thus the first joint element to the femoral component.

It is advantageous for a simple coupling of the first joint element to the femoral component if the hinge axle core projects out of the hinge axle receiver on both sides. As a result, the hinge axle core thus projects out of the second joint element in particular on both sides.

In order to at least partially protect the hinge axle core and to be able to achieve an optimal sliding pairing, in particular also with other regions or faces of the femoral component, it is advantageous if the hinge axle sleeve projects out of the hinge axle receiver on both sides.

In accordance with another preferred embodiment, provision may be made for the femoral component to have a joint receiver for accommodating the hinge joint, and for the two second connecting elements to be formed in wall faces of the joint receiver which point to each other. The wall faces pointing to each other may in particular be formed on wall sections of the femoral component that are oriented in parallel to each other and are in contact with prepared faces of the femur on their side faces pointing away from the two wall faces, to which femur the femoral component of the knee joint endoprosthesis is to be fixed. The joint receiver provides the possibility of constructing the knee joint endoprosthesis as compactly as possible and also protectively arranging the hinge joint.

The connecting device may be constructed in a simple manner if the connecting receiver is configured in the form of a groove having a groove longitudinal axis running parallel to the connecting direction. A first connecting element may thus be inserted in a simple manner into the connecting receiver in parallel to the groove longitudinal axis.

In order to be able to bring the first joint element and the femoral component into engagement in a simple manner, it is favorable if the insertion opening forms a lateral opening of the groove. The first connecting element therefore does not have to be inserted from the front in a direction toward a groove base of the groove, but rather may be inserted into the groove through the insertion opening in parallel to the groove base.

In order to be able to ensure a defined positioning of the first joint element on the femoral component, it is particularly favorable if the at least one second connecting element comprises a first stop, which is operative in the direction of the connecting direction, for the at least one first connecting element in the connecting position.

The connecting device may be constructed in a simple manner if the first stop comprises a first stop face which faces toward the insertion opening of the connecting receiver. The first stop face may in particular be formed to be planar or curved. In particular, it may be matched to an outer contour of the first joint element, for example a free end of the hinge axle or the hinge axle core. In particular, a form-fitting connection between the connecting receiver and the first stop face, on the one side, and the second connecting element may be achieved.

In accordance with another preferred embodiment, provision may be made for the knee joint endoprosthesis to comprise a securing device for securing the connecting device in a securing position in a non-positive- and/or positive-locking manner, when the connecting device assumes the connecting position. It is to be prevented by the securing device in particular that the connecting device is unintentionally transferred from the connecting position into the assembly position. The securing device may thereby assume a securing position and namely then when the connecting device assumes the connecting position, i.e. the first and second connecting elements are engaged with each other such that the femoral component is coupled to the first joint element. The securing device may in particular be configured in the form of a screw connecting device. A direction of action of the screw connecting device may run in particular transversely, preferably perpendicularly, or parallel to the connecting direction.

The securing device may be constructed in a simple manner if it comprises at least one securing element for securing the at least one first and the at least one second connecting element in the securing position in a non-positive- and/or positive-locking manner, when they assume the connecting position. It may therefore be prevented by the at least one securing element that the first and second connecting elements, which are engaged with each other, automatically unintentionally transfer from the connecting position into the assembly position. The at least one securing element may in particular comprise an internal or external threading for securing the at least one first and the at least one second connecting element in the securing position. For example, the securing element may be configured in the form of a securing screw having an external threading section that may be screwed into a bore or a blind hole having corresponding internal threading through which the at least one first and the at least one second connecting element passes, when they assume the connecting position. A longitudinal axis of the securing element may run in particular transversely, preferably perpendicularly, or parallel to the connecting direction.

The knee joint endoprosthesis may be constructed in a particularly simple manner if the at least one securing element is configured in the form of a closure element for closing the insertion opening of the connecting receiver in the securing position. Therefore, merely the insertion opening of the connecting receiver is closed by the closure element. It is thereby prevented that the first connecting element may re-exit the connecting receiver through the insertion opening.

It is advantageous if the securing device comprises a latching or snapping connecting device for definitely fixing the at least one securing element to the at least one first or to the at least one second connecting element. With such a latching or snapping connecting device, for example, the at least one securing element may be brought into engagement with the first or the second connecting element, in particular with the connecting receiver on the femoral component, wherein the at least one securing element is automatically fixed in the securing position in a defined manner by the latching or snapping connecting device.

The at least one securing element may be fixed to one of the connecting elements in a simple manner if the latching or snapping connecting device comprises at least one first latching member and at least one second latching member cooperative therewith, which, in a latching position, are engaged in a non-positive- and/or positive-locking manner and, in a disengagement position, are disengaged, and if the at least one latching member is arranged or formed on the at least one securing element and if the at least one second latching member is arranged or formed on the at least one first or on the at least one second connecting element. A latching or snapping connecting device configured in such a way enables an automatic latching or snapping-in of the cooperative first and second latching members, when the securing element is positioned in the connecting position for securing the connecting device.

In order to improve the automatic act of bringing the first and second latching members into engagement, it is advantageous if the at least one first and the at least one second latching member are engaged under pretension when in the latching position. If they are disengaged, they are necessarily likewise pretensioned against each other, such that they, once it is possible, automatically assume the latching position.

In order, for example, to secure on both sides a first joint element in the form of a hinge axle when in the connecting position, it is favorable if the knee joint endoprosthesis comprises two securing elements. It is also conceivable to integrally form the two securing elements, such that only one single securing element is necessary in order to secure the knee joint endoprosthesis in the connecting position.

Preferably, the at least one securing element comprises a second stop, operative in the direction of the connecting direction, for the at least one first connecting element in the connecting position. The second stop ensures in particular that the first connecting element may not be unintentionally moved out of the connecting position, in particular into the mounting position.

The at least one first connecting element may be held in the connecting position in a simple and defined manner if the second stop comprises a second stop face which points in the direction toward the first stop face. For example, the at least one first connecting element may thus be held between the first and the second stop face both in the connecting position and in the securing position.

For automatically securing the at least one securing element in the securing position, it is favorable if at least one pretensioning element is associated with the at least one securing element, in order to hold the latching or snapping connecting device in the latching position under pretension. For example, the pretensioning element may be arranged or formed on the at least one securing element or on the at least one first or second connecting element.

The knee joint endoprosthesis may be produced in a particularly simple and cost-efficient manner if the at least one pretensioning element is configured in the form of a spring element. In particular, it may be configured in the form of a leaf spring.

The knee joint endoprosthesis may be constructed with particularly few parts if the at least one securing element comprises the at least one pretensioning element. The securing element may in particular be made out of a metal or out of a biocompatible plastics material.

The production of the knee joint endoprosthesis may be further simplified if the at least one securing element and the at least one pretensioning element are integrally formed.

Further, a pretensioning force may be transferred in a simple manner to the at least one first or the at least one second latching member if the at least one pretensioning element bears the at least one first or the at least one second latching member.

The latching or snapping connecting device may be constructed in a simple manner if the at least one first latching member is configured in the form of a latching projection or a latching recess, and if the at least one second latching member is formed corresponding to the at least one first latching member. For example, the latching projection may be formed on the pretensioning element in the form of a latch nose, which latching projection in the securing position engages in a latching recess, for example in the form of an offset on the first connecting element, in particular on the connecting recess.

In order to be able to secure the at least one securing element in the securing position particularly well, it is advantageous if the knee joint endoprosthesis has two first and two second latching members. In particular, a latching member may be associated with each pretensioning element.

In accordance with a preferred embodiment, provision may be made for the at least one first and the at least one second latching member to be moveable relative to each other from the disengagement position into the latching position in a securing direction and vice versa, and for the securing direction to run transversely to the connecting direction and transversely to the rotational axis. In particular, the securing direction may run perpendicularly to the connecting direction and perpendicularly to the rotational axis. Such an embodiment ensures that, for example, forces exerted by the first joint element in the direction of the connecting direction are not capable of disengaging the latching or snapping connecting device, as another force component in parallel to the securing direction would be hereby necessary. In particular, it may therefore also be achieved with the proposed further development that the parts of the knee joint endoprosthesis which are coupled to each other do not autonomously separate from each other after the implantation thereof.

Even if it is possible in principle to directly connect the tibial component and the femoral component to each other, it may be further advantageous if the knee joint endoprosthesis comprises a meniscal component which is arranged between the tibial component and the femoral component and is held on the femoral component or on the tibial component. In particular, the meniscal component may be unmovably or movably mounted on the femoral component or on the tibial component. The meniscal component, for simulating a natural knee, typically has sliding bearing faces which correspond to femoral condyles of the femoral component. Furthermore, the meniscal component may have a sliding bearing face which is cooperative with the tibial component if the meniscal component is, for example, moveably mounted on the tibial component. In particular, it may be displaceably and/or rotatably mounted on the tibial component.

In order to enable a longitudinal rotation of the tibial component relative to the femoral component as a result of a bending, i.e. a flexion of the knee, it is advantageous if the meniscal component and the tibial component are mounted so as to be rotatable relative to each other about a first rotational axis.

Furthermore, for this reason, it may be advantageous if the femoral component and the tibial component are mounted so as to be rotatable relative to each other about a second rotational axis.

The knee joint endoprosthesis may be constructed in a particularly compact manner if the first and the second rotational axis are identical. The knee joint endoprosthesis may therefore in particular be constructed in such a way that the femoral component and the tibial component are turnable relative to each other about the same mathematical axis as the meniscal component and the tibial component relative to each other.

Preferably, the second joint element is mounted on the tibial component so as to be rotatable about the second rotational axis. As a result, also the femoral component that is coupled to the tibial component by a hinge joint may be rotated or turned relative to the tibial component about the second rotational axis by means of a relative movement of the second joint element and the tibial component.

In order to enable a simple coupling of the hinge joint to the tibial component, it is advantageous if the second joint element comprises a joint pin which defines the first and/or the second rotational axis and engages in a joint pin receiver of the tibial component.

In order to enable a rotation in particular about a longitudinal axis of the tibia, it is advantageous if the joint pin is rotatably and/or displaceably held in the joint pin receiver. A displaceability enables in particular allowing a lifting off of the femoral component from the tibial component and optionally also from the meniscal component to a limited or even unlimited extent.

It is further advantageous, in particular also in the case of a knee joint endoprosthesis of the kind described hereinabove, if it comprises a luxation securing device for preventing a disengagement of the second joint element and the tibial component. In particular, it may be prevented by the luxation securing device that the femoral component and the tibial component, which are coupled to each other, become decoupled from each other in an undefined manner. The luxation securing device does not necessarily require that the connecting direction runs transversely to the rotational axis.

It is favorable in particular if the luxation securing device comprises at least one luxation securing stop for delimiting a movement of the second joint element and the tibial component relative to each other in parallel to the first and/or second rotational axis. It may thereby concern a luxation securing stop which delimits a movement of the second joint element in the direction toward the tibial component and/or away from the tibial component.

It is advantageous if the luxation securing device comprises two luxation securing stops for delimiting a movement of the second joint element and the tibial component toward each other and away from each other. With two luxation securing stops, it is thus possible in particular to non-detachably couple the second joint element and the tibial component to each other, but to allow a relative movement between both parts and thus also between the femoral component and the tibial component relative to each other to a limited extent, namely toward each other and away from each other.

In accordance with another preferred embodiment, provision may be made for the luxation securing device to comprise at least one first locking element and at least one second locking element that, in a locking position, are engaged and, in a release position, are disengaged, for the at least one first locking element to be associated with the second joint element or to be arranged or formed thereon, and for the at least one second locking element to be associated with the tibial component or to be arranged or formed thereon. With such a luxation securing device, it is possible in particular to couple, in a defined manner, the second joint element and the tibial component to each other in the locking position. In particular, such a coupling may already occur before the implantation of the tibial component, since the first joint element and the second joint element may optionally also be connected to each other after independent implantation of the femoral component and the tibial component for the coupling thereof.

In order to bring the at least one first locking element and the at least one second locking element into engagement with each other, it is favorable if these are arranged or formed so as to be moveable relative to each other. In particular, they may be arranged or formed so as to be moveable relative to each other in a locking direction transverse to the second rotational axis. Such a movability transverse to the second rotational axis may, in a simple manner, prevent a movement of the second joint element and the tibial component in parallel to the second rotational axis.

Furthermore, it is advantageous if the luxation securing device comprises a blocking element for preventing a movement of the at least one first locking element and the at least one second locking element relative to each other from the locking position into the release position. The knee joint endoprosthesis may thus be secured in the locking position by the blocking element, such that a separation of the second joint element from the tibial component is in particular not possible on the basis of the embodiment of the knee joint endoprosthesis.

In order to enable a relative movement in particular of the femoral component and the tibial component in parallel to the second rotational axis at least to a limited extent, it is favorable if the at least one first locking element and the at least one second locking element in the locking position are moveable relative to each other in a direction parallel to the second rotational axis. In particular, a movement of the locking elements relative to each other may be prevented or restricted by means of corresponding stops with cooperative stop faces.

It is advantageous if the at least one first locking element is configured in the form of a moveably mounted locking body and if the at least one second locking element is configured in the form of a locking recess in which the locking body engages in the locking position. For example, the moveably mounted locking body may be arranged or formed on the second joint element or directly or indirectly on the tibial component. Indirectly means, for example, that a further component of the knee joint endoprosthesis, which component is fixed on the tibial component, comprises the locking body or the locking recess. The locking recess may in particular be configured in the form of a circumferential annular groove which is open pointing in the direction toward the first and/or second rotational axis.

Favorably, the locking body is configured in the form of a sphere which is moveably held in a spherical bore running transversely to the second rotational axis. In particular, the spherical bore may be moveably held on the second joint element, for example on the joint pin, or on the tibial component or a further component held thereon. In particular, two, three, or more first and/or second locking elements may be provided, for example three spheres having corresponding locking recesses, in which the spheres engage, projecting out of the spherical bore.

The blocking element may be configured, in a particularly simple manner, in the form of a bolt which, in the locking position, engages in a bolt receiver of the second joint element which runs parallel or substantially parallel to the second longitudinal axis, and which bolt blocks a movement of the at least one first locking element in the direction toward the first and/or second rotational axis. In particular, the bolt receiver may be formed on the joint pin. This embodiment enables in particular implanting the femoral component and the tibial component independently of each other and coupling them in the tibial component by bringing the second joint element into engagement with the joint element receiver, wherein the connection between the tibial component and the femoral component is securable by means of the blocking element engaging in the joint pin.

It is favorable for the handling of the knee joint endoprosthesis during implantation if the bolt receiver is configured in the form of a blind hole which is open pointing in the direction toward the femoral component. This embodiment enables in particular inserting the blocking element into the bolt receiver in a direction parallel to the first and/or second rotational axis in order to thus couple the femoral component and the tibial component to each other. In particular, it is not necessary in the case of a blocking element, as it was described above, to provide a locking cone on the bolt, which locking cone cooperates with a corresponding locking cone on the bolt receiver in order to couple the femoral component to the tibial component. A blind hole also has the advantage that the blocking element does not need to project out over the joint pin in the direction toward the femoral component and extend said joint pin.

In order to prevent that the blocking element unintentionally becomes detached and the luxation securing device is thereby unintendedly transferred into the release position, it is favorable if the bolt is configured to be screwable into the bolt receiver. In practice, such a screwable bolt practically does not become detached from the bolt receiver.

As already mentioned, the at least one second locking element does not have to be arranged or formed directly on the tibial component. It is favorable if the at least one second locking element is arranged or formed on a locking sleeve and if the locking sleeve is held in the joint pin receiver in a non-positive- and/or positive-locking manner. Providing such a locking sleeve has in particular the advantage that the at least one second locking element is arrangeable at different positions. In particular, the knee joint endoprosthesis may be modularly configured and a position of the at least one second locking element on the tibial component may be individually adjusted according to the patient. In addition, one may optionally also individually specify a displaceability of the second joint element in the joint pin receiver. For that purpose, the entire tibial component does not need to be correspondingly formed, but rather a knee joint endoprosthesis that is optimal for a patient may be formed with a standard tibial component and a selection of various locking sleeves.

Favorably, the locking sleeve is held in the joint pin receiver by a retaining element. The retaining element therefore serves in particular to fix the locking sleeve at least axially on the femoral component. This means that the locking sleeve is not moveable or is moveable to a limited extent in parallel to the first and/or second rotational axis.

The knee joint endoprosthesis may be constructed in a simple manner if the retaining element is configured in the form of a retaining sleeve and to be screwable to the joint pin receiver so as to surround the locking sleeve. For example, the retaining sleeve may be configured in the form of a cap nut or a screwable insert.

In accordance with another preferred embodiment, provision may be made for the joint pin receiver to define a first locking sleeve stop, and for the retaining element to define a second locking sleeve stop, and for the locking sleeve to be held in the joint pin receiver by the first and the second locking sleeve stop. The locking sleeve stops thus prevent in particular a movement of the locking sleeve in the joint pin receiver in parallel to the first and/or second rotational axis. Thy may in particular be configured such that the locking sleeve is not displaceable in the joint pin receiver or such that it is limitedly displaceable.

It is advantageous if the femoral component and the tibial component are fully separated from each other in the assembly position and if they are, starting from the assembly position, coupleable to each other, after a mutually independent implantation of the femoral component and the tibial component, by coupling the at least one first and the at least one second connecting element to each other. This embodiment enables an individual implantation of femoral component and tibial component, wherein limitations do not exist in the case of a coupling of the two components already before the implantation.

In order to enable a defined rotation of the meniscal component relative to the tibial component, it is advantageous if the tibial component has a pivot bearing element for mounting the meniscal component so as to be rotatable about the first rotational axis.

Preferably, the first pivot bearing element is configured in the form of a pin protruding from the tibial component. Said pin may in particular be configured in the shape of a sleeve and may extend into the joint pin receiver. The knee joint endoprosthesis may thus be constructed in a particularly compact manner.

An embodiment of a knee joint endoprosthesis that is designated as a whole with the reference numeral 10 is schematically depicted in the figures. It comprises a tibial component 14, which is fixable on a tibia 12, and a femoral component 18, which is fixable on a femur 16.

After the implantation of the knee joint endoprosthesis, 10, the tibial component and the femoral component 18 are coupled by a hinge joint 20 so as to be pivotal about a rotational axis 22.

The hinge joint 20 comprises a first joint element 24 and a second joint element 26 which is coupled therewith so as to be turnable about the rotational axis 22.

The tibial component 14 comprises a shank 28 which is insertible into a cavity of the tibia 12 and is fixable therein. Said shank 28 may optionally be configured modularly with extensions of different lengths which are not depicted in the figures, such that the tibial component 14 may, depending on the physiology of the patient, be optimally anchored in their tibia 12.

The tibial component 14 further comprises a plate 30 from the underside 32 away from which the shank 28 extends perpendicularly or substantially perpendicularly. An upper side 34 of the plate 30 forms a planar joint face 36 on which an meniscal component, which is optionally comprised by the knee joint endoprosthesis 10, lies with its underside 40, which defines a planar contact face 42.

The meniscal component 38 is moveably mounted on the plate 30. For this purpose, the tibial component 14 has a pivot bearing element 44 for mounting the meniscal component 38 so as to be rotatable about a first rotational axis 46. Said first rotational axis 46 is defined by the first pivot bearing element 44 which is configured in the form of a pin 48 protruding perpendicularly from the upper side 34. Said pin 48 juts into a pin receiver 50 which is formed correspondingly thereto and which is in the form of an opening in a meniscal component 38. In this way, the meniscal component 38 is mounted on the plate 30 so as to be turnable about the first rotational axis 46.

The meniscal component 38 has on its upper side 52 two joint faces 54 on which condyle faces 56, pointing from the femoral component 18 in the direction toward the tibial component 14, abut and slide when the femoral component 18 is turned relative to the tibial component 14 about the rotational axis 22.

The femoral component 14 has further a box-like joint receiver 58 that is delimited by two walls 60 running parallel to each other. The walls 60 have wall faces 62 which point toward each other and which run perpendicularly to the rotational axis 22.

Furthermore, a backside 64 of the femoral component 18 is provided with a multitude of bone contact faces 66 having recesses in the form of cement pockets in order to place the femoral component 18 on prepared bone faces of the femur 16 and fix it thereto, in particular with bone cement.

Optionally, the femoral component 18 may be coupled with a shank which is not depicted in the Figures. For this purpose, an opening 70 is formed on a further wall 68 which delimits the joint receiver 58 and runs transversely to the walls 16, which opening 70 is passed through by a connecting element or may be coupled to an extension shank for insertion into a cavity of the femur 16.

The first joint element 24 defines the rotational axis 22 with its longitudinal axis. It is configured in the form of a hinge axle 72 which passes through a corresponding hinge axle receiver 74 of the second joint element 26. The hinge axle receiver 74 is configured in the form of a through-bore at an end section 78 of the second joint element 26 facing the femoral component 18. The hinge axle 72 and the hinge axle receiver 74 form a sliding bearing 80.

The hinge axle 72, which overall has the form of an elongated circular cylinder, comprises a hinge axle core 82 and a hinge axle sleeve 84 surrounding said hinge axle core 82. An outer face 86 of the hinge axle sleeve 84 as well as an inner face 88 of the hinge axle receiver 74 thus define sliding faces of the sliding bearing 80.

In order to construct a best possible, low-wear sliding pairing, the materials of the second joint element 26 and the hinge axle sleeve 84 may thus be optimally matched to each other. For example, the hinge axle sleeve 84 may be made out of a plastics material, the second joint element 26 out of an instrument steel.

In an embodiment depicted in the Figures, the hinge axle core 82 has a circular cross section. The hinge axle sleeve 84 may be coupled to the hinge axle core 82 by a press fit seating.

Alternatively, the hinge axle core may also have a non-round cross section, for example an oval or an angular, in particular a rectangular or hexagonal, cross section. A cross section of a hinge axle core receiver 90 of the hinge sleeve 84 then preferably has a corresponding cross section, such that the hinge axle sleeve 84 is non-rotatably connected to the hinge axle core 82 if the cross section of the hinge axle core 82 is non-round.

In the embodiment depicted in the Figures, the hinge axle core 82 projects out of the hinge axle sleeve 84 on both sides. In this way, free ends 92 of the hinge axle core 82 form connecting projections 94.

As easily recognized for example in FIG. 12, the hinge axle core 82 also juts out of the hinge axle receiver 74 on both sides.

Furthermore, the hinge axle sleeve 84 also projects out of the hinge axle receiver 74 on both sides.

A sliding bearing plate 96 sits on both sides of the end section 78 on the hinge axle sleeve 84 projecting out of the hinge axle receiver 74. Said sliding bearing plate 96 may be made in particular out of the same material as the hinge axle sleeve 84. Side faces 98, pointing away from each other, of the sliding bearing plates 96 abut on the wall faces 62.

The joint receiver 58 has in the wall faces in each case one connecting receiver 100, which is configured in the form of a groove 102, that defines a groove longitudinal axis 104 that runs transversely, in particular perpendicularly, to the rotational axis 22.

The groove is open at its end remote from the wall 68 and defines an insertion opening 106.

The connecting projections 94 form first connecting elements 108, and the connecting receivers 100 form second connecting elements 110 of a connecting device, which is designated as a whole with the reference number 112, for connecting the first joint element 24 to the femoral component 18.

The connecting device 112 is configured in such a way that it defines a connecting position in which the first connecting elements 108 and the second connecting elements 110 are engaged in a non-positive- and/or positive-locking manner. This connecting position is schematically depicted for example in FIGS. 12 and 14.

Further, the connecting device 112 defines an assembly position in which the first joint element 24 and the femoral component 18 are fully separated from each other. The connecting elements 108 and 110 are disengaged in this position. The assembly position is depicted for example in FIG. 9.

The first connecting elements 108 are associated with the first joint element 24 and are arranged or formed thereon, respectively. The second connecting elements 110 are associated with the femoral component 185 and are arranged or formed thereon, respectively.

The connecting device 112 further defines a connecting direction 114 in which the first connecting elements 108 and the second connecting elements 110 are moveable relative to each other for transferring the connecting device 112 from the assembly position into the connecting position. The connecting direction is defined by the groove longitudinal axis 104 because the connecting projections 94 can be inserted into the connecting receivers 110 only in parallel to the groove longitudinal axis 104. As a result, the connecting direction 114 also runs transversely, namely perpendicularly to the rotational axis 22.

Due to the particular embodiment of the knee joint endoprosthesis 10, the hinge axle core 82 is, in the connecting position, engaged with the second connecting element 110 in a non-positive- and/or positive-locking manner.

The second connecting elements 110 have a first stop 116, which is operative in the direction of the connecting direction 114, for the first connecting elements 108 in the connecting position. The first stop 116 is formed by a first stop face 118 which points in the direction toward the insertion opening 106 of the connecting receiver 100. In the connecting position, as is depicted in FIG. 14, the connecting projection 94 abuts on the first stop face 118.

In order to secure the first and second connecting element 108, 110, which are engaged with each other, a securing device 120 is provided for securing the connecting device 112 in a securing position, which is depicted for example in FIG. 14, in a non-positive- and/or positive-locking manner, when the connecting device 112 assumes the connecting position. The securing device 120 comprises two securing elements 122 for securing the first and second connecting elements 108, 110 in the securing position in a non-positive- and/or positive-locking manner when they assume the connecting position.

The securing elements 122 are configured in the form of closure elements 124 for closing the insertion opening 106 of the connecting receiver 100 in the securing position. The closure elements are configured to be substantially parallelepipedal and comprise a second stop 126 for the second connecting element 110. The second stop 126 comprises a second stop face 128 that points in the direction toward the first stop ace 118. As may be easily seen in FIG. 14, the first connecting element 108 is, in the connecting position, held between the two stop faces 118 and 128.

So that the securing elements 122 may not exit the connecting recess 100 as a result of a force acting on the hinge axle 72, the securing device 120 comprises a latching or snapping connecting device 130 for fixing the securing elements 122 to the second connecting element 110 in a defined manner.

The securing element 122 comprises a substantially parallelepipedal stop body 132 on which the second stop face 128 is formed.

In parallel to the connecting direction 114 extend pretensioning elements 134 that hold the latching or snapping connecting device 130, subsequently referred to only as latching connecting device, under pretension when in the latching position depicted in FIG. 14.

The latching connection device 130 comprises first latching members 136, which are configured in the form of latching projections 138, that, in the latching position, engage in corresponding latching recesses 140 that define second latching members 142. As may be seen in FIG. 14, the first and second latching members 136, 142 are engaged in a non-positive- and/or positive-locking manner in the latching position.

The projections 138 are each arranged on a support 144 from which actuating projections, which point from the support 144 in the direction toward the insertion opening 106 in parallel to the pretensioning element 134, protrude. If the two actuating projections 146 are moved toward each other in the direction of the arrow 148 and 150, the latching projections 138 release the latching recesses 140, such that the latching connecting device 130 assumes a disengagement position which is not depicted in the Figures.

The first latching members 136 are thus arranged on the securing element 122, the second latching members formed on the second connecting elements 110. The latching recesses 140 point toward each other and are formed in groove side walls 152 of the groove 102 which point toward each other.

The pretensioning elements 134 are configured in the form of spring elements 154, namely as leaf springs 156. These hold the latching connecting device 130 under pretension when in the latching position. In the embodiment depicted in the Figures, the securing element 122 comprises two pretensioning elements 134 and is preferably integrally formed therewith. The securing element 122 may in particular be made out of a metal or a plastics material.

Due to the arrangement of the latching projections 138 on the supports 144, each pretensioning element 134 also bears a first latching member 136.

Furthermore, the latching connecting device 130 is configured in such a way that the first and second latching members 136 and 142 are moveable relative to each other in a securing direction 158 from the disengagement position into the latching position and vice versa. The securing direction 158 runs transversely to the connecting direction 114 and transversely to the rotational axis 22. In the embodiment of the knee joint endoprosthesis 10 depicted in the Figures, the securing direction 158, the rotational axis 22, and the connecting direction 114 each run perpendicularly to each other.

In order to hold the sliding bearing plates 96 in the joint receiver 58 so as to be secured against rotation, on each sliding bearing plate 96 is formed a projection 160 pointing in the direction toward the wall face 62, the projection 160 engaging in a corresponding recess 162 in the walls 60 in the connecting position.

Further, the knee joint endoprosthesis 10 is configured such that the femoral component 18 and the tibial component 14 are mounted so as to be rotatable or turnable relative to each other about a second rotational axis 164. In the embodiment depicted in the Figures, the first and the second rotational axis 46, 164 are identical.

The second joint element 26 is mounted on the tibial component 14 so as to be rotatable about the second rotational axis 164. How this is achieved will be subsequently described in detail.

The second joint element 26 comprises a joint pin 166 which protrudes from the end section 78 and is integrally formed therewith. Said joint pin 166 defines the first and the second rotational axis 46, 164 and engages in a joint pin receiver 168 of the tibial component 14. The joint pin receiver 168 is configured in the form of a blind hole 170 and is closed by a blind hole base 172 on its end pointing away from the femoral component 18.

In order to be able to turn the femoral component 18 and the tibial component 14 relative to each other about the rotational axes 46 and 164, the joint pin 166 is rotatably mounted in the joint pin receiver 168.

Furthermore, in the embodiment depicted in the Figures, the joint pin 166 is held in the joint pin receiver 168 so as to also be displaceable in parallel to the rotational axes 46 and 164. The latter is achieved in particular by a luxation securing device 174. This prevents a disengagement of the second joint element 26 and the tibial component 14.

As is subsequently described in detail, the second joint element 26 is coupleable to the tibial component 14 and may also be permanently held thereon.

Into the joint pin receiver 168 is inserted a locking sleeve 176 that bears an annular projection that points away from the rotational axis 46 in radial direction. The annular projection 178 is insertable so far into joint pin receiver 168 until it strikes a first locking sleeve stop 180 that is formed by a single-stage cross section tapering of the joint pin receiver 168.

The pivot bearing element 44 also delimits the joint pin receiver 168 and is thus formed in the shape of a sleeve. Starting from an end of the pivot bearing element 44 which points in the direction toward the femoral component 18, said pivot bearing element 44 is provided with an internal threading section 182 which corresponds to an external threading section 184 of a retaining sleeve 186. An annular projection 188, which is formed on the end of the retaining sleeve 186 which faces the femoral component 18, and which points away from the rotational axis 46 in radial direction, forms a depth stop for screwing the retaining sleeve 186 into the joint pin receiver 168.

An annular end face 190 of the retaining sleeve 186 which points away from the femoral component 18 forms a second locking sleeve stop 192 for the annular projection 178. As a result, a movement of the locking sleeve 176 in the direction toward the femoral component 18 is delimited by the second locking stop 192, and is delimited in the direction into the joint pin receiver 168 by the first locking sleeve stop 180.

An annular groove 194 that is open in the direction toward the rotational axis 46 is formed on the locking sleeve 176 in its interior, about at the level of the annular projection 178.

The retaining sleeve 186 forms a retaining element 196 for holding the locking sleeve 176 in the joint pin receiver 168.

The luxation securing device 174 comprises a first luxation securing stop 198 and a second luxation securing stop 200 for delimiting a movement of the second joint element 26 and the tibial component 14 relative to each other in parallel to the rotational axes 46 and 164. The luxation securing stops 198, 200 are formed by groove side faces 202 and 204 of the annular groove 194 which point substantially toward each other. The groove side face 202 thereby delimits a movement of the second joint element 26 away from the tibial component 14, the groove side face 204 delimits a movement of the second joint element 26 into the joint pin receiver 168.

The luxation securing device 174 further comprises first and second locking elements 206 and 208 that, in a locking position, are engaged and, in a release position, are disengaged.

In the embodiment depicted in the Figures, three first locking elements 206 and one second locking element 208 are provided. The first locking elements 206 are thereby associated with and arranged on the second joint element 26, respectively, and the second locking elements 208 is associated with the tibial component 14 and is arranged or formed thereon, respectively.

The first locking elements 206 are configured in the form of moveably mounted locking bodies 210. The second locking element 208 is configured in the form of a locking receiver 212.

In a locking position, as it is depicted for example in FIG. 8, the locking body 210 engages in the locking receiver 212. The locking receiver 212 is formed by the annular groove 194. Each locking body 210 is configured in the form of a sphere 214 which is moveably held in a spherical bore 216 running transversely to the second rotational axis 164.

A diameter of the sphere 214 is smaller than a spacing of the groove side faces 202 and 204 from each other, so that the first locking elements 206 and the second locking element 208 in the locking position, in which the locking elements 206 and 208 are engaged, are moveable in a direction parallel to the second rotational axis 164.

The locking elements 206 and 208 are moveable relative to each other as described, namely in a locking direction 218 that runs transversely to the second rotational axis 164. In particular, the spheres 214 may be moved in the spherical bores 216 in radial direction away from the rotational axis 164 or towards it.

Furthermore, the luxation securing device 174 comprises a blocking element 220 for preventing a movement of the first locking elements 206 and the second locking element 208 relative to each other from the locking position into a release position in which they are disengaged.

The blocking element 220 is configured in the form of a bolt 222 which, in the locking position, engages in a bolt receiver 224 of the joint element 26, which bolt receiver 224 runs parallel or substantially parallel to the second rotational axis 164. The bolt receiver 224 extends into the joint pin axis 160. Said joint pin 160 is closes at its end 226 pointing way from the femoral component 18, so that the bolt 222 may not lengthen the joint pin.

The bolt receiver 224 is configured in the form of a blind hole 228 which is open pointing in the direction toward the femoral component 18.

The bolt 222 has on its end facing the femoral component 18 a head 230 having a tool element receiver 232 in the form of a polygonal socket or an internal multi-round. An external threading section 234 connects to the head 230, which external threading section 234 corresponds to an internal threading section 236 of the blind hole 228, starting from its end pointing in the direction toward the femoral component 18. By means of this configuration, the bolt 222 is screwable into the bolt receiver 224.

In the region of it distal end, the bolt 222 fills out the bolt receiver 224 in cross section, so that the spheres 214 are hindered from moving in the direction to the second rotational axis 164.

The knee joint endoprosthesis 10 allows a surgeon to first fix the tibial component 14 and the femoral component 18 independently of each other to the tibia 12 and the femur 16, respectively. Before the implantation of the tibial component 14, the hinge joint 20 is coupled to the tibial component 14. For this purpose, the joint pin 166 is inserted into the joint pin receiver 168 and is transferred into the locking position, in which the spheres 214 engage in the annular groove 194, by screwing the bolt 222 into the bolt receiver 224 of the luxation securing device.

For coupling the femoral component 18 and the tibial component 14 to each other, the first and second connecting elements 108 and 110 are now brought into engagement with each other, namely by inserting the hinge axle 72 into the connecting receivers 100 in the manner already described hereinabove. For securing the connecting device in the connecting position, the two securing elements 122 of the securing device 120 are finally inserted into the connecting receivers 100 in the described manner until the latching members 136 and 132 engage in each other.

For adapting the knee joint endoprosthesis 10 to different physiologies of patients, meniscal components 38 of different heights may be provided. In order to achieve an optimal connection of the tibial component 14 to the femoral component 18, either different second joint elements 26 with joint pins 166 of different lengths may then be provided and/or different locking sleeves 176 in which the annular groove 194 is arranged differently at a distance from and end of the locking sleeve 176 which points in the direction toward the femoral component. Modular knee joint endoprostheses may thus be produced in a simple manner, wherein merely corresponding pairs of meniscal components 38 and locking sleeves 176 need to be provided in order to allow the surgeon to individually adjust the knee joint endoprosthesis 10 to the respective needs of a patient.

REFERENCE NUMERAL LIST

10 Knee joint endoprosthesis
12 tibia
14 tibia component 16 femur
18 femoral component
20 hinge joint
22 rotational axis
24 first joint element
26 second joint element
28 shank
30 plate
32 underside
34 upper side
36 joint face
38 meniscal component
40 underside
42 contact face
44 pivot bearing element
46 first rotational axis
48 pin
50 pin receiver
52 upper side
54 joint face
56 condyle face
58 joint receiver
60 wall
62 wall face
64 backside
66 bone contact face
68 wall
70 opening
72 hinge axle
74 hinge axle receiver
76 through-bore
78 end section
80 sliding bearing
82 hinge axle core
84 hinge axle sleeve
86 outer face
88 inner face
90 hinge axle receiver
92 free end
94 connecting projection
96 sliding bearing plate
98 side face
100 connecting receiver
102 groove
104 groove longitudinal axis
106 insertion opening
108 first connecting element
110 second connecting element
112 connecting device
114 connecting direction
116 first stop
118 first stop face
120 securing device
122 securing element
124 closure element
126 second stop
128 second stop face
130 latching or snapping connecting device
132 stop body
134 pretensioning element
136 first latching member
138 latching projection
140 latching recess
142 second latching member
144 support
146 actuating projection
148 arrow
150 arrow
152 groove side wall
154 spring element
156 leaf spring
158 securing direction
160 projection
162 recess
164 second rotational axis
166 joint pin
168 joint pin receiver
170 blind hole
172 blind hole base
174 luxation securing device
176 locking sleeve
178 annular projection
180 first locking sleeve stop
182 internal threading section
184 external threading section
186 retaining sleeve
188 annular projection
190 end face
192 second locking sleeve stop
194 annular groove
196 retaining element
198 first luxation securing stop
200 second luxation securing stop
202 groove side face
204 groove side face
206 first locking element
208 second locking element
210 locking body
212 locking receiver
214 sphere
216 spherical bore
218 locking direction
220 blocking element
222 bolt
224 bolt receiver
226 end
228 blind hole
230 head
232 tool element receiver
234 external threading section
236 internal threading section

What is claimed is:

1. A knee joint endoprosthesis comprising:
a tibial component and a femoral component,
a hinge joint for coupling the tibial component and the femoral component so as to be pivotal about a rotational axis,
the hinge joint comprising a first joint element and a second joint element coupled therewith so as to be rotatable about the rotational axis,
a connecting device comprising at least one first connecting element and at least one second connecting element for connecting the first joint element to the femoral component,
the connecting device defining:
a connecting position, in which the at least one first connecting element and the at least one second connecting element are engaged in at least one of a non-positive-locking manner and a positive-locking manner, and
an assembly position, in which the first joint element and the femoral component are fully separated from each other, wherein:
the at least one first connecting element is associated with the first joint element or is arranged or formed thereon,
the at least one second connecting element is associated with the femoral component or is arranged or formed thereon,
the connecting device defines a connecting direction, in which the at least one first connecting element and the at least one second connecting element are moveable relative to each other for transferring the connecting device from the assembly position into the connecting position,
the connecting direction runs transversely to the rotational axis,
the at least one first connecting element is configured in the form of a connecting projection and the at least one second connecting element is configured in the form of a connecting receiver, or vice versa, and
the connecting receiver extends in parallel to the connecting direction and has an insertion opening for the insertion of the connecting projection in parallel to the connecting direction.

2. The knee joint endoprosthesis in accordance with claim 1, wherein at least one of:
a) the second joint element is held on the tibial component or is coupleable therewith, and
b) the connecting device is configured in such a way that it is transferrable from the assembly position into the connecting position after a mutually independent implantation of the femoral component and the tibial component, and
c) a longitudinal axis defined by the first joint element defines the rotational axis, and
d) the knee joint endoprosthesis comprises at least one of two first and two second connecting elements.

3. The knee joint endoprosthesis in accordance with claim 1, wherein the first joint element is configured in the form of a hinge axle, and wherein the second joint element has a hinge axle receiver that is passed through by the hinge axle.

4. The knee joint endoprosthesis in accordance with claim 3, wherein at least one of:
a) the hinge axle receiver is configured in the form of a through-bore, and
b) the hinge axle and the hinge axle receiver form a sliding bearing.

5. The knee joint endoprosthesis in accordance with claim 3, wherein the hinge axle comprises a hinge axle core and a hinge axle sleeve arranged or mounted on the hinge axle core.

6. The knee joint endoprosthesis in accordance with claim 5, wherein at least one of:
a) the hinge axle and the hinge axle receiver form a sliding bearing, and the hinge axle sleeve and the hinge axle receiver define the sliding bearing, and
b) the hinge axle core in the connecting position is engaged with the at least one second connecting element in at least one of a non-positive-locking and a positive-locking manner, and
c) the hinge axle core has a circular, oval, or an angular, cross section,
or
the hinge axle core has a circular, oval, rectangular or hexagonal cross section.

7. The knee joint endoprosthesis in accordance with claim 5, wherein at least one of:
a) the hinge axle sleeve has a hinge axle core receiver for accommodating the hinge axle core, and wherein the hinge axle core receiver has a free cross section corresponding to the hinge axle core, and
b) the hinge axle core projects out of the hinge axle sleeve on both sides, and
c) the hinge axle core projects out of the hinge axle receiver on both sides, and
d) the hinge axle sleeve projects out of the hinge axle receiver on both sides.

8. The knee joint endoprosthesis in accordance with claim 1, wherein the at least one second connecting element comprises a first stop, which is operative in the direction of the connecting direction, for the at least one first connecting element in the connecting position.

9. The knee joint endoprosthesis in accordance with claim 1, further comprising a securing device for securing the connecting device in a securing position in at least one of a non-positive-locking and a positive-locking manner when the connecting device assumes the connecting position, and wherein the securing device comprises at least one securing element for securing the at least one first and the at least one second connecting element in the securing position in at least one of a non-positive-locking and a positive-locking manner when they assume the connecting position.

10. The knee joint endoprosthesis in accordance with claim 9, wherein at least one of:
a) the at least one securing element is configured in the form of a closure element for closing the insertion opening of the connecting receiver in the securing position, and
b) the securing device comprises a latching or snapping connecting device for fixing the at least one securing element to the at least one first or to the at least one second connecting element in a defined manner, the latching or snapping connecting device comprises at least one first latching member and at least one second latching member cooperative therewith, which, in a latching position, are engaged in at least one of a non-positive-locking and a positive-locking manner and, in a disengagement position, are disengaged, and wherein the at least one first latching member is arranged or formed on the at least one securing element, and wherein the at least one second latching member is arranged or formed on the at least one first or on the at least one second connecting element, and
c) the knee joint endoprosthesis comprises two securing elements.

11. The knee joint endoprosthesis in accordance with claim 10, wherein the at least one securing element comprises a second stop, which is operative in the direction of the connecting direction, for the at least one first connecting element in the connecting position.

12. The knee joint endoprosthesis in accordance with claim 11, wherein:
the at least one second connecting element comprises a first stop, which is operative in the direction of the connecting direction, for the at least one first connecting element in the connecting position,
the first stop comprises a first stop face, and
the second stop comprises a second stop face pointing in the direction toward the first stop face.

13. The knee joint endoprosthesis in accordance with claim 9, wherein the securing device comprises a latching or snapping connecting device for fixing the at least one securing element to the at least one first or to the at least one second connecting element in a defined manner, the latching or snapping connecting device comprises at least one first latching member and at least one second latching member cooperative therewith, which, in a latching position, are engaged in at least one of a non-positive-locking and a positive-locking manner and, in a disengagement position, are disengaged, and wherein the at least one first latching member is arranged or formed on the at least one securing element, and wherein the at least one second latching member is arranged or formed on the at least one first or on the at least one second connecting element, wherein at least one pretensioning element is associated with the at least one securing element in order to hold the latching or snapping connecting device under pretension when in the latching position.

14. The knee joint endoprosthesis in accordance with claim 13, wherein at least one of:
   a) the at least one pretensioning element is configured in the form of a spring element,
   or
   the at least one pretensioning element is configured in the form of a leaf spring, and
   b) the at least one securing element comprises the at least one pretensioning element.

15. The knee joint endoprosthesis in accordance with claim 13, wherein at least one of:
   a) the at least one securing element and the at least one pretensioning element are integrally formed, and
   b) the at least one pretensioning element bears the at least one first or the at least one second latching member.

16. The knee joint endoprosthesis in accordance with claim 1, wherein at least one of:
   a) the knee joint endoprosthesis comprises a meniscal component which is arranged between the tibial component and the femoral component, held on the femoral component or the tibial component,
   or
   the knee joint endoprosthesis comprises a meniscal component which is arranged between the tibial component and the femoral component, and held moveably mounted on the femoral component or the tibial component, and
   b) the meniscal component and the tibial component are mounted so as to be rotatable relative to each other about a first rotational axis, and
   c) the second joint element comprises a joint pin which defines at least one of the first and the second rotational axis and engages in a joint pin receiver of the tibial component.

17. The knee joint endoprosthesis in accordance with claim 1, further comprising a luxation securing device for preventing a disengagement of the second joint element and the tibial component.

18. The knee joint endoprosthesis in accordance with claim 17, wherein the luxation securing device comprises at least one first locking element and at least one second locking element that, in a locking position, are engaged and, in a release position, are disengaged, wherein the at least one first locking element is associated with the second joint element or is arranged or formed thereon, and wherein the at least one second locking element is associated with the tibial component or is arranged or formed thereon.

19. The knee joint endoprosthesis in accordance with claim 18, wherein at least one of:
   a) the at least one first locking element and the at least one second locking element are arranged or configured so as to be moveable relative to each other,
   or
   the femoral component and the tibial component are mounted so as to be rotatable relative to each other about a second rotational axis and the at least one first locking element and the at least one second locking element are arranged or configured so as to be moveable relative to each other in a locking direction transverse to the second rotational axis, and
   b) the luxation securing device comprises a blocking element for preventing a movement of the at least one first locking element and the at least one second locking element relative to each other from the locking position into the release position, and
   c) the femoral component and the tibial component are mounted so as to be rotatable relative to each other about a second rotational axis and the at least one first locking element and the at least one second locking element in the locking position are moveable relative to each other in a direction parallel to the second rotational axis, and
   d) the at least one first locking element is configured in the form of a moveably mounted locking body, and wherein the at least one second locking element is configured in the form of a locking receiver in which the locking body engages in the locking position, and
   e) the at least one second locking element is arranged or formed on a locking sleeve, and wherein the locking sleeve is held in the joint pin receiver in at least one of a non-positive-locking and a positive-locking manner.

20. The knee joint endoprosthesis in accordance with claim 1, wherein the knee joint endoprosthesis comprises a meniscal component which is arranged between the tibial component and the femoral component, held:
   a) on the femoral component or the tibial component, wherein the tibial component has a pivot bearing element for mounting the meniscal component so as to be rotatable about the first rotational axis,
or
   movably mounted on the femoral component or the tibial component, wherein the tibial component has a pivot bearing element for mounting the meniscal component so as to be rotatable about the first rotational axis.

21. The knee joint endoprosthesis in accordance with claim 1, wherein the connecting receiver is configured in the form of a groove having a groove longitudinal axis running parallel to the connecting direction.

22. The knee joint endoprosthesis in accordance with claim 21, wherein the insertion opening forms a lateral opening of the groove.

23. The knee joint endoprosthesis in accordance with claim 1, wherein the connecting direction runs perpendicularly to the rotational axis.

* * * * *